US007060495B2

(12) United States Patent
Gehrmann et al.

(10) Patent No.: US 7,060,495 B2
(45) Date of Patent: Jun. 13, 2006

(54) FUSION PROTEINS FOR PRODRUG ACTIVATION

(75) Inventors: Mathias Gehrmann, Lollar (DE); Gerhard Seemann, Marburg (DE); Klaus Bosslet, Marburg (DE); Jörg Czech, Marburg (DE)

(73) Assignee: Behrinwerke Aktienegesellschaft, Marburg (DE)

( * ) Notice: Subject to any disclaimer, the term of this patent is extended or adjusted under 35 U.S.C. 154(b) by 0 days.

(21) Appl. No.: 08/989,896

(22) Filed: Dec. 12, 1997

(65) Prior Publication Data

US 2002/0068329 A1 Jun. 6, 2002

Related U.S. Application Data

(62) Division of application No. 08/475,826, filed on Jun. 7, 1995, now abandoned, which is a division of application No. 08/404,949, filed on Mar. 15, 1995, now abandoned, which is a continuation of application No. 08/129,379, filed on Sep. 30, 1993, now abandoned.

(30) Foreign Application Priority Data

Oct. 2, 1992 (DE) .......................................... 42 33 152

(51) Int. Cl.
*A61K 39/395* (2006.01)
*C07K 16/00* (2006.01)

(52) U.S. Cl. ................................ 435/387.3; 424/134.1; 424/135.1; 424/137.1; 424/155.1; 424/178.1; 424/182.1; 435/69.7; 435/252.33; 435/254.2; 435/254.21; 530/387.5; 530/388.5; 530/391.1

(58) Field of Classification Search ............... 424/134.1, 424/135.1, 137.1, 155.1, 178.1, 182.1; 435/69.7, 435/252.33, 254.2, 254.21; 530/387.3, 387.5, 530/388.5, 391.1
See application file for complete search history.

(56) References Cited

U.S. PATENT DOCUMENTS

| 4,870,009 | A |   | 9/1989 | Evans et al. ................ 435/69.4 |
| 4,873,316 | A |   | 10/1989 | Meade et al. ................ 530/412 |
| 5,132,405 | A |   | 7/1992 | Huston et al. ........... 430/387.3 |
| 5,258,498 | A | * | 11/1993 | Huston et al. .............. 530/350 |
| 5,591,828 | A | * | 1/1997 | Bosslet et al. ........... 530/387.3 |
| 5,869,045 | A | * | 2/1999 | Hellstrom et al. ....... 424/130.1 |
| 6,248,516 | B1 | * | 6/2001 | Winter et al. ................. 435/6 |
| 6,258,360 | B1 | * | 7/2001 | von Borstel et al. ..... 424/182.1 |

FOREIGN PATENT DOCUMENTS

| CA |   | 2019559 |   | 12/1990 |
| CA | A | 2062047 |   | 8/1992 |
| EP |   | 0302473 | A2 | 2/1989 |
| EP |   | 0361908 | A2 | 4/1990 |
| EP |   | 0382411 | A2 | 8/1990 |
| EP |   | 0392745 | A2 | 10/1990 |
| EP |   | 0404097 | A2 | 12/1990 |
| EP |   | 0501215 | A2 | 9/1992 |
| WO | WO | 88/07378 |   | 10/1988 |
| WO | WO | 89 10140 |   | 11/1989 |
| WO | WO | 91/00108 |   | 1/1991 |
| WO | WO | 91/08770 |   | 6/1991 |
| WO | WO | 91/11201 |   | 8/1991 |
| WO |   | 9313805 | * | 7/1993 |

OTHER PUBLICATIONS

Ong et al, Cancer Research, 51, 1619–1626, 1991.*
Huston et al, Methods in Enzthology, 203, 46–89, 1991.*
I. Hellstrom et al., "Antitumor effects of L6, and IgG2a antibody that reacts with most human carcinomas," Proc. Natl. Acad. Sci. USA, vol. 83, pp. 7059–7063 (1986).
I. Hellstrom et al., "Monoclonal mouse antibodies raised against human lung carcinoma," Cancer Res, vol. 46, No. 8, pp. 3917–3923 (1986).
C. A. Janeway, Jr., et al., *"Immuno Biology The Immune System in Health and Disease,"* Current Biology Ltd/Garland Publishing Inc., New York, pp. 12:33–12:36 (1994).
Perham, R.N., "Domains, Motifs, and Linkers in 2–Oxo Acid Dehydrogenase Multienzyme Complexis: A Paradigm in the Design of a Multifunctional Protein." *Biochemistry*, 30:8501–8512, 1991.
Fremont, D.H., et al., "Biophysical Studies of T–cell receptors and Their Ligands." *Curr. Opin. Immunol.*, 8:93–100, 1996.
Brocklehurst, S., "Re: Linker Peptide in Two–domain fusion Protein," [http://www.bio.net//hypermail/protein–analysis/proteins. 199307/0048.html], Jul. 26, 1993.
Osband, Immunol. Today, 11(6): 193–195, 1990.
Chatterjee, Cancer Immunol. Immunother., 38:75–82.
Curti, Crit. Rev. Oncol. Hematol., 14:29–39, 1993.
Jain, Sci, America, 271(1):58–63, 1994.
Kerr, D.E., et al., "Antibody–penicillin–V–amidase conjugates kill antigen–positive tumor cells when combined with doxorubicin phenoxyacetamide", Cancer Immuno. Immunother, vol. 31: 202–206 (1990).
Florent, J.C. et al., "N–(–D–Glycopyranosyl)–Benzyloxycarbonyl Daunorubicine Pro–Prodrugs Synthesis and enzymatic behaviour", inst. Carbohydr. Symp. Paris, A262, p. 297 (1992).
Andrianomenjanahary, S. et al., "N–(–D–Glycopyranosyl)–Chlorobenzyloxycarbonyl Daunorubicine Pro–Prodrugs and their enzymatic cleavage", Inst. Carbohydro. Symposium Paris, A264, p. 299 (1992).

(Continued)

*Primary Examiner*—David Saunders
(74) *Attorney, Agent, or Firm*—Karen I. Krupen

(57) ABSTRACT

The invention relates to compounds which contain an antigen binding region which is bound to at least one enzyme which is able to metabolize a compound (prodrug) which has little or no cytotoxicity to a cytotoxic compound (drug), where the antigen binding region is composed of a single polypeptide chain. It is advantageous for covalently bonded carbohydrates to be present on the polypeptide chain.

23 Claims, 20 Drawing Sheets

OTHER PUBLICATIONS

Goochee, C.F. et al., "The Oligosaccharides of Glycoproteins; Bioprocess Factors Affecting Oligosaccharide Structure and Their Effect on Glycoprotein Properties", Biotechnology, vol. 9:1347–1355 (1991).

Gussow, D. et al., "Humanization of Monoclonal Antibodies", Methods in Enzymology, vol. 203:99–121 (1991).

Jefferson, R.A. et al., "B–Glucuronidase from *Escherichia coli* as a gene–fusion marker", Proc. Natl. Acad. Sci. USA, vol. 83: 8447–8451 (1986).

Hussain, M. et al., "Cloning and Sequencing of the Metallothioprotein B–Lactamase II Gene of *Bacillus cereus* 569/H in *Escherichia coli*", Journal of Bacteriology, vol. 164:22–229 (1985).

Sharma, S.K. et al., "Inactivation and clearance of an anti–CEA carboxypeptidase G2 conjugate in blood after localisation in a xenograft model", Br. J. Cancer, vol. 61: 659–662 (1990).

Bosslet, K. et al., "Molecular and functional characterisation of a fusion protein suited for tumour specific prodrug activation," British Journal of Cancer, 65(2): 234–238 (1992).

Brinkmann, Ulrich et al., "Independent domain folding of Pseudomonas exotoxin and single–chain immunotoxins: Influence of interdomain connections," Proceedings of the National Academy of Sciences of the USA, 89(7): 3075–3079 (1992).

Kappel, C. et al. (1992). Current Opinion: Biotechnology, 3:548–53.

Shamay, A. et al. (1991) J. Animal Science, 69: 4552–62.

Borden, T. et al. (1991) Mechanisms of Development, 36: 67–74.

* cited by examiner pAB-Back:

5'  
ACC AGA AGC TTA TGA ATA TGC AAA TC  3' (SEQ ID NO:3)

Linker-Anti:

5'  
GCC ACC CGA CCC ACC ACC GCC CGA TCC ACC GCC TCC TGA

GGA GAC GGT GAC CGT GGT C  3' (SEQ ID NO:4)

Linker-Sense:

5'  
GGT GGA TCG GGC GGT GGT GGG TCG GGT GGC GGC GGA TCT

GAC ATC CAG CTG ACC CAG AGC  3' (SEQ ID NO:5)

V_L(Mut)-For:

5'  
TGC AGG ATC CAA CTG AGG AAG CAA AGT TTA AAT TCT ACT

CAC CTT TGA TC  3' (SEQ ID NO:6)

FIG. 2

Replacement Sheet

Oligos for sFv 431/26 cloning in pUC19 sFv for (2561)
5'  TTT TTA AGC TTA GAT CTC CAC CTT GGT C   3'
(SEQ ID NO:7)

sFv back (2577)
5'  AAA AAT CTA GAA TGC AGG TCC AAC TGC AGG
    AGA G   3'  (SEQ ID NO:8)

Oligos for hum.β-Gluc cloning in sFv pUC19

Hum.β-Gluc. back oligo (2562)
5'  AAA AAA GTC ATC AAA GCG TCT GGC GGG CCA CAG
    GGC GGG ATC CTG TAC   3'  (SEQ ID NO:9)

Hum.β-Gluc. for oligo (2540)
5'  TTT TAA GCT TCA AGT AAA CGG GCT GTT   3'
(SEQ ID NO:10)

Oligos for sFv/hum-β-Gluc cloning in sFv pIXY120

PCR oligo VHpIXY (2587)
5'  TTT TGG TAC CTT TGG ATA AAA GAC AGG TCC AAC TGC AGG
    AGA G   3'  (SEQ ID NO:11)

PCR oligo VKpIXY FOR (2627)
5'  A AAA CCA TGG GAA TTC AAG CTT CGA GCT GGT ACT ACA
    GGT   3'  (SEQ ID NO:12)

FIG. 8

OLIGOS FOR E.coli β-Gluc CLONING IN sFv pUC19

*E.coli* β-Gluc. FOR (2639)

5' TTT TAA GCT TCC ATG GCG GCC GCT CAT TGT TTG
   CCT CCC TGC TG   3'   (SEQ ID NO:13)

*E.coli* β-Gluc. BACK (2638)

5' AAA AAG ATC TCC GCG TCT GGC GGG CCA CAG TTA
   CGT GTA GAA ACC CCA   3'   (SEQ ID NO:14)

FIG. 13

Oligos FOR sFv/β-lactamase CLONING IN pIXY120

PCR oligo VHpIXY BACK (2587)
5' TTT TGG TAC CTT TGG ATA AAA GAC AGG TCC AAC TGC AGG
   AGA G   3'   (SEQ ID NO:15)

PCR oligo VKpIXY/β-lactamase for (2669)
5' AAA AAG CTT AGA TCT CCA GCT TGG TCC C   3'
(SEQ ID NO:16)

PCR oligo link/β-lactamase back (2673)
5' AAA GAA TTC TGA TCA AAT CCT CGA GCT CAG GTT CAC
   AAA AGG TAG AGA AAA CAG T   3' linker (SEQ ID NO:17)

PCR oligo β-lactamase for (2674)
5' TTT AAG CTT ATT TTA ATA AAT CCA ATG T   3'
(SEQ ID NO:18)

*FIG. 16*

FUSION PROTEINS FOR PRODRUG ACTIVATION

REFERENCE TO RELATED APPLICATIONS

This application is a divisional of U.S. application Ser. No. 08/475,826, filed Jun. 7, 1995, (abandoned), which is a divisional of U.S. application Ser. No. 08/404,949, filed Mar. 15, 1995, now abn, which is a continuation of U.S. application Ser. No. 08/129,379, filed Sep. 30, 1993, now abn.

BACKGROUND OF THE INVENTION

The invention relates to compounds which contain an antigen binding region which is bound to at least one enzyme which is able to metabolize a compound (prodrug) which has little or no cytotoxicity to a cytotoxic compound (drug), where the antigen binding region is composed of a single polypeptide chain. It is advantageous for covalently bonded carbohydrates to be present on the polypeptide chain.

The combination of prodrug and antibody-enzyme conjugates for use as therapeutic composition has already been described in the specialist literature. This entails antibodies which are directed against a particular tissue and to which a prodrug-cleaving enzyme is bound being injected into an organism, and subsequently a prodrug compound which can be activated by the enzyme being administered. The action of the antibody-enzyme conjugate bound to the target tissue is intended to convert the prodrug compound into a compound which exerts a cytotoxic effect on the bound tissue. However, studies on antibody-enzyme conjugates have shown that these chemical conjugates have unfavorable pharmacokinetics so that there is only inadequate site-specific tumor-selective cleavage of the prodrug. Some authors have attempted to remedy this evident deficiency by additional injection of an anti-enzyme antibody which is intended to bring about rapid elimination of the anti-body-enzyme conjugate from the plasma (Sharma et al., Brit. J. Cancer, 61, 659, 1990). Another problem of antibody-enzyme conjugates is the limited possibility of preparing large amounts reproducibly and homogeneously.

The object of the present invention was now to find fusion proteins which can be prepared on an industrial scale and are suitable, by reason of their pharmacokinetic and pharmacodynamic properties, for therapeutic uses.

It has been found in this connection that compounds which contain an antigen binding region which is composed of a single polypeptide chain have unexpected advantages for the preparation and use of fusion proteins, to which carbohydrates are advantageously attached, in prodrug activation.

The invention therefore relates to compounds which contain an antigen binding region which is bound to at least one enzyme, where the antigen binding region is composed of a single polypeptide chain, and carbohydrates are advantageously attached to the fusion protein.

BRIEF DESCRIPTION OF THE DRAWINGS

FIG. 2 shows the nucleotide sequences of oligonucleotides pAB-Back, linker-anti, linker-sense, and $V_{L(Mut)}$-For.

FIG. 3 is a schematic representation of the amplification of the $V_H$ gene, including the signal sequence intrinsic to the $V_H$ gene, from the plasmid pABstop 431$V_H$hum ($V_H$ 431/26) by PCR using oligonucleotides pAB-Back and linker-anti, and the amplification of the $V_H$ gene from pABstop 431$V_L$hum ($V_L$ 431/26) by PCR using oligonucleotides linker-sense and $V_{L(Mut)}$-For.

FIG. 8 shows the nucleotide sequences of oligonucleotides sFv for (2561), sFv back (2577), Hum.β-Gluc. back oligo (2562), Hum.β-Gluc. for oliqo (2540), PCR oligo VHpIXY back (2587), and PCR oligo VKpIXY for (2627).

FIG. 13 shows the nucleotide sequences of oligonucleotides E. coli β-Gluc. for (2639) and E. coil β-Gluc. back (2638).

FIG. 16 shows the nucleotide sequences of oligonucleotides PCR oligo VHpIXY back (2587), ECR oligo VKpIXY/β-lactamase for (2669), PCR oligo link/β-lactamase back (2673), and PCR oligo β-lactamase for (2674).

Figure 1:
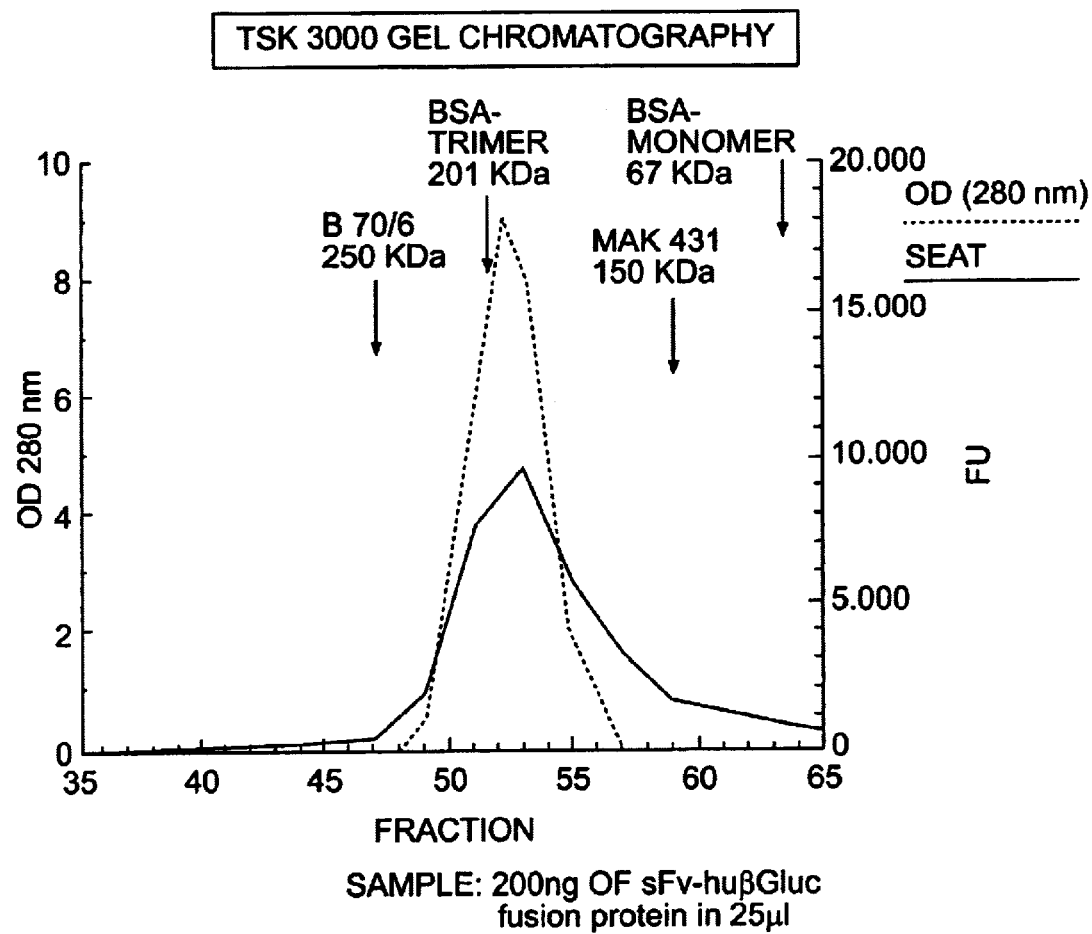
FIG. 1 demonstrates the purification of the sFv-huβ-Gluc fusion protein by TSK 3000 qel chromatography.

An antigen binding region means for the purpose of the invention a region which contains at least two variable domains of an antibody, preferably one variable domain of a heavy antibody chain and one variable domain of a light antibody chain (sFv fragment). The antigen binding region can, however, also have a bi- or multivalent structure, i.e. two or more binding regions, as described, for example, in EP-A-0 404 097. However, a human or humanized sFv fragment is particularly preferred, especially a humanized sFv fragment.

The antigen binding region preferably binds to a tumor-associated antigen (TAA), with the following TAAs being particularly preferred:

neural cell adhesion molecule (N-CAM),
polymorphic epithelial mucin (PEM),
epidermal growth factor receptor (EGF-R),
Thomsen Friedenreich antigen β (TFβ),
gastrointestinal tract carcinoma antigen (GICA),
ganglioside $GD_3$ $(GD_3)$,
ganglioside $GD_2$ $(GD_2)$,
Sialyl-Le$^a$, Sialyl-Le$^x$,
TAG72,
the 24–25 kDa glycoprotein defined by MAb L6,
CA 125 and, especially,
carcinoembryonic antigen (CEA).

Preferred enzymes are those enzymes which are able to metabolize a compound of little or no cytotoxicity to a cytotoxic compound. Examples are β-lactamase, pyroglutamate aminopeptidase, galactosidase or D-aminopeptidase as described, for example, in EP-A2-0 382 411 or EP-A2-0 392 745, an oxidase such as, for example, ethanol oxidase, galactose oxidase, D-amino-acid oxidase or α-glyceryl-phosphate oxidase as described, for example, in WO 91/00108, peroxidase as disclosed, for example, in EP-A2-0 361 908, a phosphatase as described, for example, in EP-A1-0 302 473, a hydroxynitrilelyase or glucosidase as disclosed, for example, in WO 91/11201, a carboxypeptidase such as, for example, carboxypeptidase G2 (WO 88/07378), an amidase such as, for example, penicillin 5-amidase (Kerr, D. E. et al. Cancer Immunol. Immunther. 1990, 31) and a protease, esterase or glycosidase such as the already mentioned galactosidase, glucosidase or a glucuronidase as described, for example, in WO 91/08770.

A β-glucuronidase is preferred, preferably from *Kobayasia nipponica* or *Secale cereale,* and more preferably from *E. coli* or a human β-glucuronidase. The substrates for the individual enzymes are also indicated in the said patents and are intended also to form part of the disclosure content of the present application. Preferred substrates of βglucuronidase are N-(D-glycopyranosyl)benzyloxycarbonylanthracyclines and, in particular, N-(4-hydroxy3-nitrobenzyloxycarbonyl) doxorubicin and daunorubicin β-D-glucuronide (J. C. Florent et al. (1992) Int. Carbohydr. Symp. Paris, A262, 297 or S. Andrianomenjanahary et al. (1992) Int. Carbohydr. Symp. Paris, A 264, 299).

The invention further relates to nucleic acids which code for the compounds according to the invention. Particularly preferred is a nucleic acid, as well as its variants and mutants, which codes for a humanized sFv fragment against CEA (carcinoembryonic antigen) linked to a human β-glucuronidase, preferably with the nucleotide sequence of SEQ ID NO:1, which codes for the amino acid sequence of SEQ ID NO2 (sFv-huβ-Gluc).

The compounds according to the invention are prepared in general by methods of genetic manipulation which are generally known to the skilled worker, it being possible for the antigen binding region to be linked to one or more enzymes either directly or via a linker, preferably a peptide linker. The peptide linker which can be used is, for example, a hinge region of an antibody or a hinge-like amino-acid sequence. In this case, the enzyme is preferably linked with the N terminus to the antigen binding region directly or via a peptide linker. The enzyme or enzymes can, however, also be linked to the antigen binding region chemically as described, for example, in WO 91/00108.

The nucleic acid coding for the amino-acid sequence of the compounds according to the invention is generally cloned in an expression vector, introduced into prokaryotic or eukaryotic host cells such as, for example, BHK, CHO, COS, HeLa, insect, tobacco plant, yeast or *E.coli* cells and expressed. The compound prepared in this way can subsequently be isolated and used as diagnostic aid or therapeutic agent. Another generally known method for the preparation of the compound according to the invention is the expression of the nucleic acids which code therefor in transgenic mammals with the exception of humans, preferably in a transgenic goat.

BHK cells transfected with the nucleic acids according to the invention express a fusion protein (sFv-huβ-Gluc) which not only was specific for CEA but also had full β-glucuronidase activity (see Example 5).

This fusion protein was purified by anti-idiotype affinity chromatography in accordance with the method described in EP 0 501 215 A2 (Example M). The fusion protein purified in this way gives a molecular weight of 100 kDA in the SDS PAGE under reducing conditions, while molecules of 100 and 200 kDa respectively appear under non-reducing conditions.

Gel chromatography under native conditions (TSK-3000 gel chromatography) showed one protein peak (Example 6, FIG. I) which correlates with the activity peak in the specificity enzyme activity test (EP 0 501 215 A2). The position of the peak by comparison with standard molecular weight markers indicates a molecular weight of ≈200 kDa. This finding, together with the data from the SDS PAGE, suggests that the functional enzymatically active sFv-huβ-Gluc fusion protein is in the form of a "bivalent molecule", i.e. with 2 binding regions and 2 enzyme molecules. Experiments not described here indicate that the fusion protein may, under certain cultivation conditions, be in the form of a tetramer with 4 binding regions and 4 enzyme molecules. After the sFv-huβ-Gluc fusion protein had been purified and undergone functional characterization in vitro, the pharmacokinetics and the tumor localization of the fusion protein were determined in nude mice provided with human gastric carcinomas. The amounts of functionally active fusion protein were determined in the organs and in the tumor at various times after appropriate workup of the organs (Example 7) and by immunological determination (triple determinant test, Example 8). The results of a representative experiment are compiled in Table 1.

Astonishingly, a tumor/plasma ratio of 5/1 is reached after only 48 hours. At later times, this ratio becomes even more favorable and reaches values >200/1 (day 5). The reason for this favorable pharmacokinetic behavior of the sFv-huβ-Gluc fusion protein is that fusion protein not bound to the tumor is removed from the plasma and the normal tissues by internalization mainly by receptors for mannose 6-phosphate and galactose. (Evidence for this statement is that there is an intracellular increase in the β-glucuronidase level, for example in the liver).

As shown in Table 2, the sFv-huβ-Gluc contains relatively large amounts of galactose and, especially, mannose, which are mainly responsible for the binding to the particular receptors. The fusion protein/receptor complex which results and in which there is binding via the carbohydrate residues of the fusion protein is then removed from the extracellular compartment by internalization.

This rapid internalization mechanism, which is mainly mediated by galactose and mannose, is closely involved in the advantageous pharmacokinetics of the fusion protein according to the invention. These advantageous pharmacokinetics of the fusion protein to which galactose and, in particular, mannose are attached makes it possible for a hydrophilic prodrug which undergoes extracellular distribution to be administered i.v. at a relatively early time without eliciting non-specific prodrug activation. In this case an elimination step as described by Sharma et al. (Brit. J. Cancer, 61, 659, 1990) is unnecessary. Based on the data in Table 1, injection of a suitable prodrug (S. Adrianomenjanahari et al. 1992, Int. Carbohydrate Symp., Parts A264, 299) is possible even 3 days after injection of the sFv-huβ-Gluc fusion protein without producing significant side effects (data not shown).

A similarly advantageous attachment of carbohydrates to fusion proteins can also be achieved, for example, by secretory expression of the sFv-huβ-Gluc fusion protein in particular yeast strains such as *Saccharomyces cerevisiae* or *Hansenula polymorpha*. These organisms are capable of very effective mannosylation of fusion proteins which have appropriate N-glycosylation sites (Goochee et al., Biotechnology, 9, 1347–1354, 1991). Such fusion proteins which have undergone secretory expression in yeast cells show a high degree of mannosylation and favorable pharmacokinetics comparable to those of the sFv-huβ-Gluc fusion protein expressed in BHK cells (data not shown). In this case, the absence of galactose is compensated by the even higher degree of mannosylation of the fusion protein (Table 3). The sFv-huβ-Gluc fusion protein described above was constructed by genetic manipulation and expressed in yeast as described in detail in Example 9.

Instead of human β-glucuronidase it is, however, also possible to employ another glucuronidase with advantageous properties. For example, the *E.coli* β-glucuronidase has the particular advantage that its catalytic activity at pH 7.4 is significantly higher than that of human β-glucuronidase. In Example 10, an sFv-*E.coli* β-Gluc construct was prepared by methods of genetic manipulation and underwent secretory expression as functionally active mannosylated fusion protein in *Saccharomyces cerevisiae*. The pharmacokinetic data are comparable to those of the sFv-huβ-Gluc molecule which was expressed in yeast or in BHK cells (Table 1).

The glucuronidases from the fungus *Kobayasia nipponica* and from the plants *Secale cereale* have the advantage, for example, that they are also active as monomers. In Example 11, methods of genetic manipulation were used to prepare a construct which, after expression in *Saccharomyces cerevisiae*, excretes an sFv-*B. cereus* β-lactamase II fusion protein preferentially in mannosylated form.

This fusion protein likewise has, as the fusion proteins according to the invention, on the basis of β-glucuronidase pharmacokinetics which are favorable for prodrug activation (Table 1).

Furthermore, the compounds according to the invention can be employed not only in combination with a prodrug but also in the framework of conventional chemotherapy in which cytostatics which are metabolized as glucuronides and thus inactivated can be converted back into their toxic form by the administered compounds.

The following examples now describe the synthesis by genetic manipulation of sFv-β-Gluc fusion proteins, and the demonstration of the ability to function.

The starting material comprised the plasmids pABstop 431/26 hum $V_H$ and pABstop 431/26 hum $VH_L$. These plasmids contain the humanized version of the $V_H$ gene and $V_L$ gene of anti-CEA MAb BW 431/26 (Güssow and Seemann, 1991, Meth. Enzymology, 203, 99–121). Further starting material comprised the plasmid pABstop 431/26 $V_H$-huβ-Gluc 1H (EP-A2-0 501 215) which contains a $V_H$ exon, including the $V_H$-intrinsic signal sequence, followed by a CH1 exon, by the hinge exon of a human IgG3 C gene and the complete cDNA of human β-glucuronidase.

EXAMPLE 1

Amplification of the $V_H$ and $V_L$ Genes of MAb hum 431/26

Figure 3:
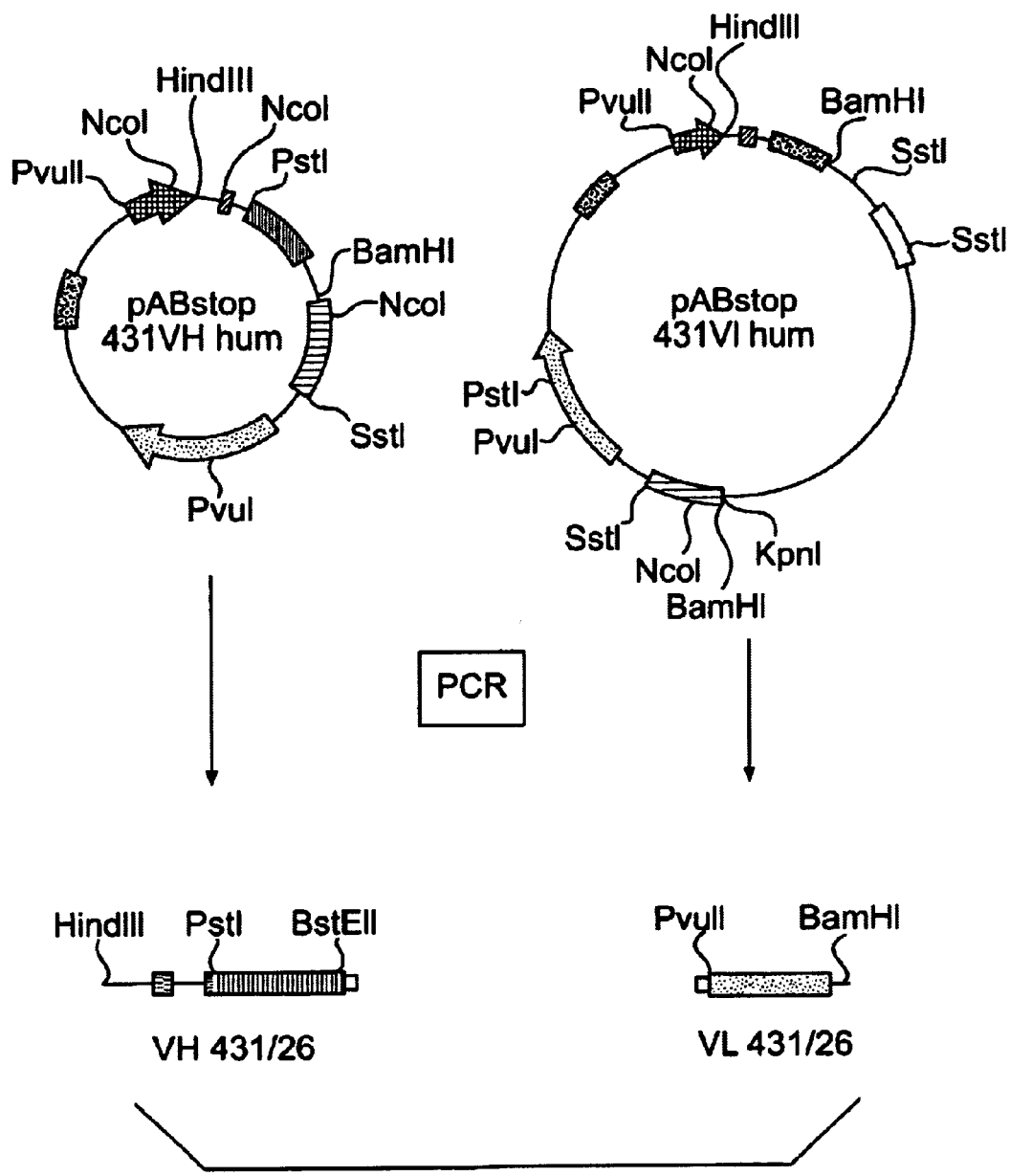

The oligonucleotides pAB-Back (SEQ ID NO:3) and linker-anti (SEQ ID NO:4) (FIG. 2) are used to amplify the $V_H$ gene including the signal sequence intrinsic to the $V_H$ gene from pABstop 431$V_H$ hum ($V_H$ 431/26) (FIG. 3) (Güssow and Seemann, 1991, Meth. Enzymology, 203, 99–121). The oligonucleotides linker-sense (SEQ ID NO:5) and $V_{L(Mut)}$-For (SEQ ID NO:6) (FIG. 2) are used to amplify the $V_L$ gene from pABstop 431$V_L$ hum ($V_L$ 431/26) (FIG. 3).

EXAMPLE 2

Joining of the $V_H$ 431/26 and $V_L$ 431/26 Gene Fragments

The oligonucleotides linker-anti and linker-sense are partially complementary with one another and encode a polypeptide linker which is intended to link the $V_H$ domain and $V_L$ domain to give an sFv fragment. In order to fuse the amplified $V_H$ fragments with the $V_L$ fragments, they are purified and employed in a 10-cycle reaction as follows:

| | |
|---|---|
| H₂O: | 37.5 μl |
| dNTPs (2.5 mM): | 5.0 μl |
| PCR buffer (10×): | 5.0 μl |
| Taq polymerase (Perkin-Elmer Corp., Emmeryville, CA) (2.5 U/μl): | 0.5 μl |
| 0.5 μg/μl DNA of the $V_L$ frag.: | 1.0 μl |
| 0.5 μg/μl DNA of the $V_H$ frag.: | 1.0 μl |

PCR buffer (10×): 100 mM tris, pH 8.3, 500 mM KCl, 15 mM MgCl2, 0.1% (w/v) gelatin.

Figure 4:
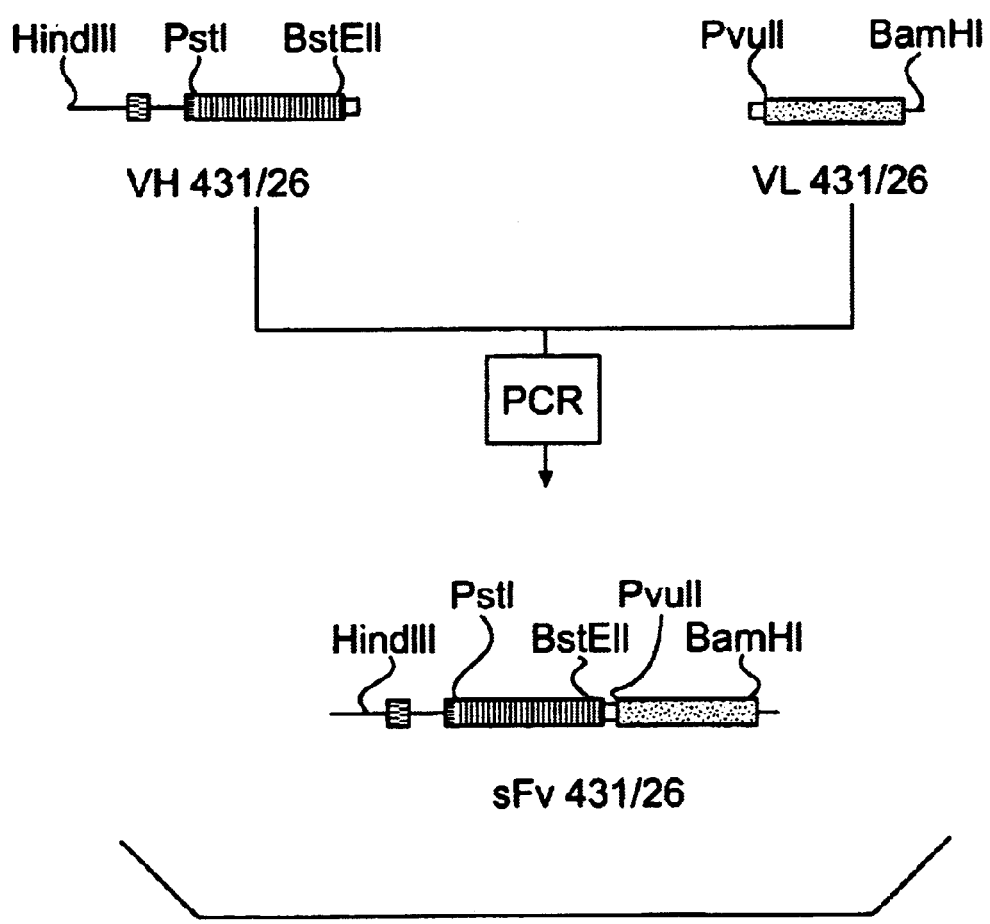
FIG. 4 is a schematic representation of the amplification and fusion of the $V_H$431/26 and the $V_L$431/26 gene fragments by PCR.

The surface of the reaction mixture is sealed with paraffin, and subsequently the 10-cycle reaction is carried out in a PCR apparatus programmed for 94° C., 1 min; 55° C., 1 min; 72° C., 2 min. 2.5 pmol of the flanking primer pAB-Back and $V_{L(Mut)}$-For are added, and a further 20 cycles are carried out. The resulting PCR fragment is composed of the $V_H$ gene which is linked to the $V_L$ gene via a linker (FIG. 4). The signal sequence intrinsic to the $V_H$ gene is also present in front of the $V_H$ gene. The oligonucleotide $V_{L(Mut)}$-For also results in the last nucleotide base of the $V_L$ gene, a C, being replaced by a G. This PCR fragment codes for a humanized single-chain Fv (sFv 431/26).

EXAMPLE 3

Cloning of the sFv 431/26 Fragment into the Expression Vector Which Contains the huβ-glucuronidase Gene.

Figure 5:
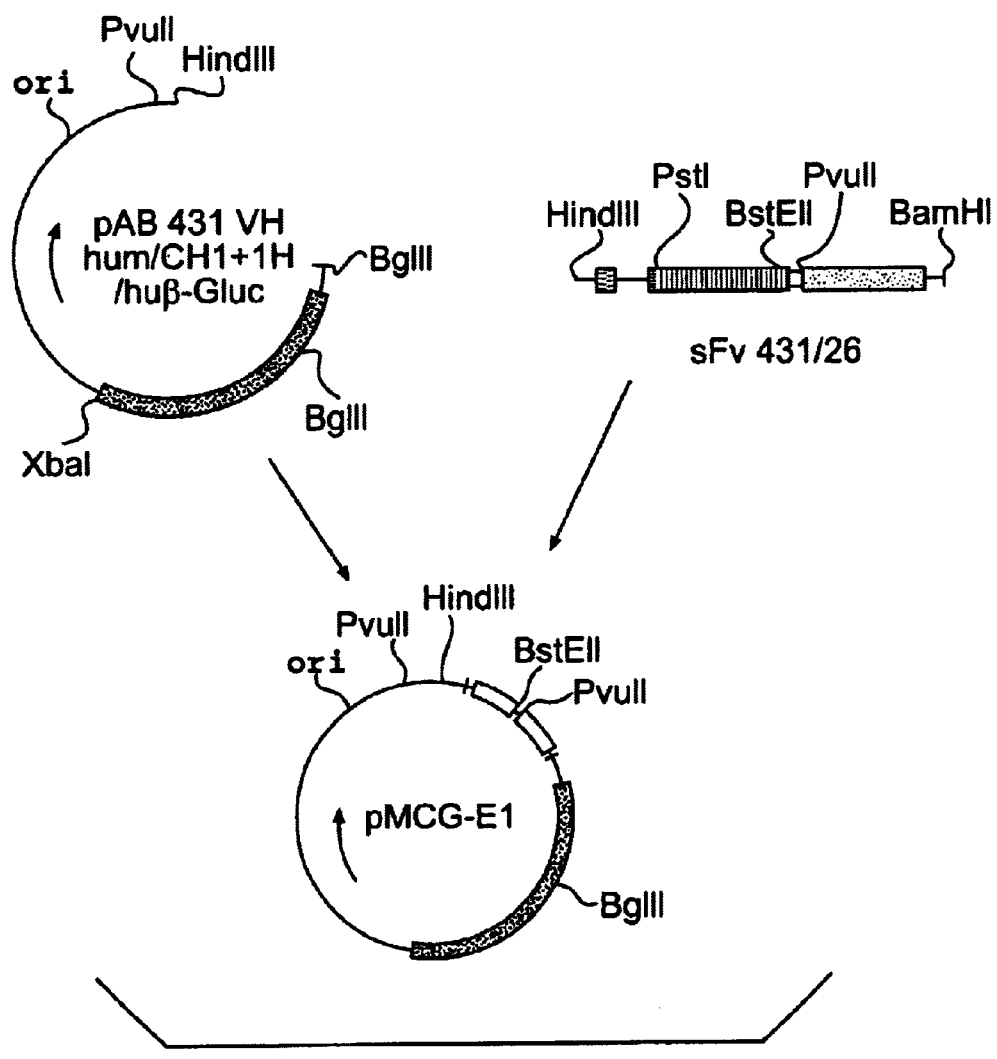
FIG. 5 is a schematic representation of the cloning of the sFv 431/26 fragment into the expression vector pAB 431$V_H$hum/$C_H$1+1H/β-Glc, which contains the huβ-glucuronidase gene.

The sFv fragment from (2) is cut with HindIII and BamHI and ligated into the vector pAB 431$V_H$ hum/CH1+1h/β-Glc which has been completely cleaved with HindIII and partially cleaved with BglII. The vector pABstop 431/26$V_H$huβ-Gluc1H contains a $V_H$ exon, including the $V_H$-intrinsic signal sequence, followed by a CH1 exon, by the hinge exon of a human IgG3 C gene and by the complete cDNA of human β-glucuronidase. The plasmid clone pMCG-E1 which contains the humanized sFv 431/26, a hinge exon and the gene for human β-glucuronidase is isolated (pMCG-E1). (FIG. 5)

EXAMPLE 4
Expression of the sFv-huβ-Gluc Fusion Protein in BHK Cells.

Figure 6:
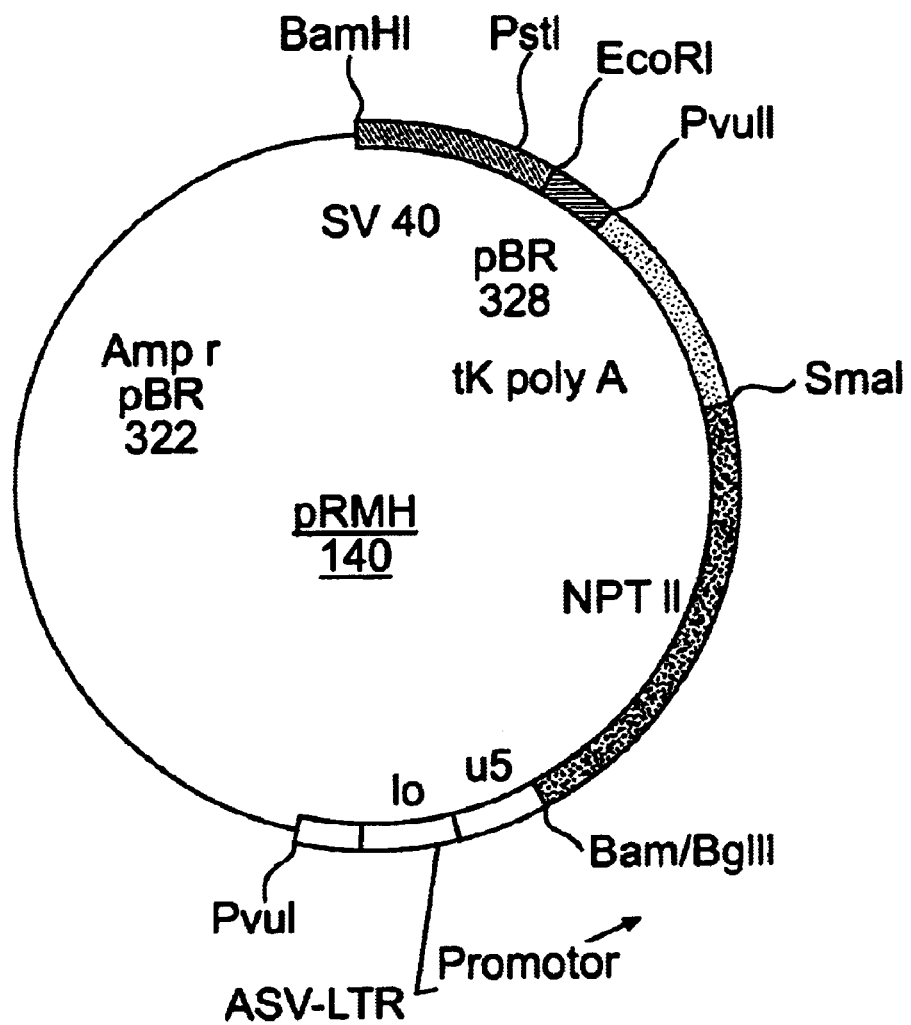
FIG. 6 is a schematic representation of the plasmid pRMH 140, which harbors a neomycin-resistance gene.
Figure 7:
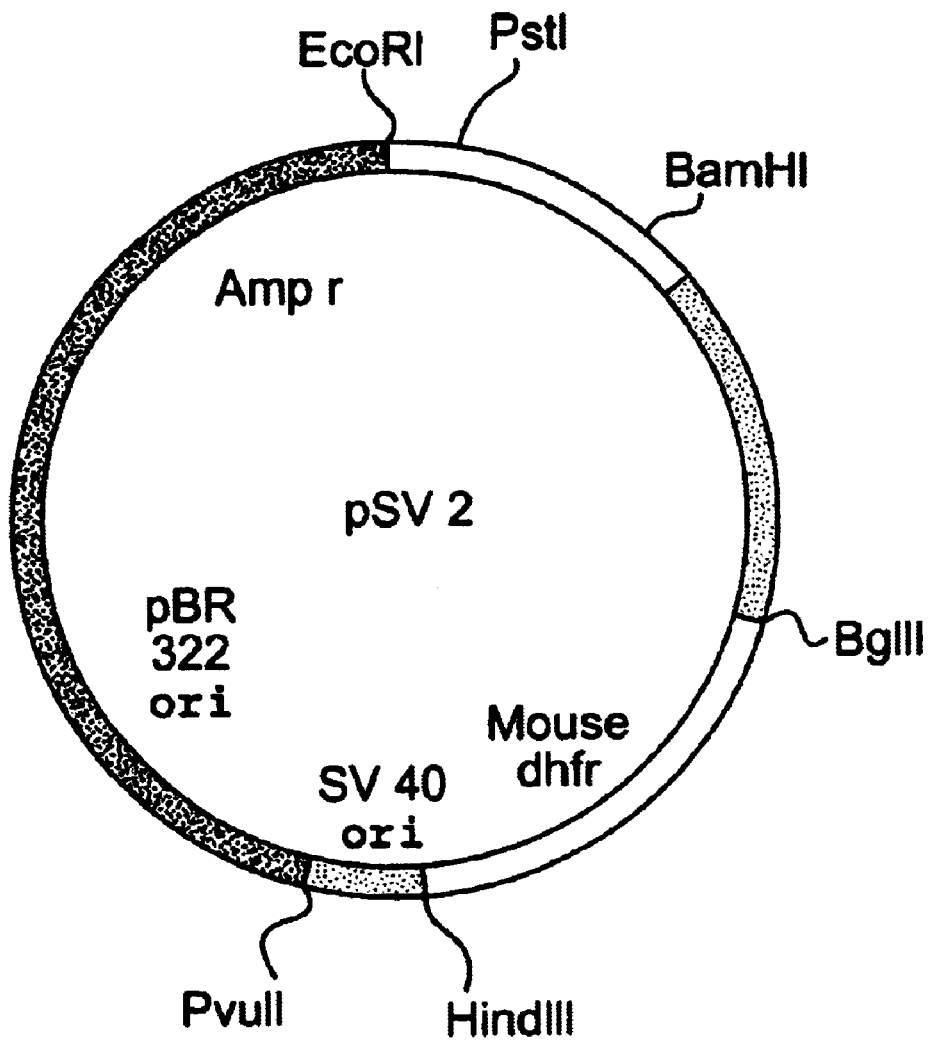
FIG. 7 is a schematic representation of the plasmid pSV2, which harbors a methotrexate-resistance gene.

The clone pMCG-E1 is transfected with the plasmid pRMH 140 which harbors a neomycin-resistance gene (FIG. 6) and with the plasmid pSV2 which harbors a methotrexateresistance gene (FIG. 7) into cells. The BHK cells subsequently express a fusion protein which has both the antigen-binding properties of MAb BW 431/26hum and the enzymatic activity of human β-glucuronidase.

EXAMPLE 5
Demonstration of the Antigen-binding Properties and of the Ensymatic Activity of the sFv-huβ-Gluc Fusion Protein.

The ability of the sFv-huβ-Gluc fusion protein to bind specifically to the CEA epitope defined by 431/26 and simultaneously to exert the enzymatic activity of human β-glucuronidase was shown in a specificity enzyme activity test (EP-A2-0 501 215). The test determines the liberation of 4-methylumbelliferone from 4-methylumbelliferyl β-glucuronide by the β-glucuronidase portion of the fusion protein after the fusion protein has been bound via the sFv portion to an antigen. The measured fluorescence values are reported as relative fluorescence units (FU). The test shows a significant liberation of methyl-umbelliferone by the fusion protein in the plates coated with CEA. By contrast, the fusion protein does not liberate any methylumbelliferone in control plates coated with PEM (polymorphic epithelial mucin).

EXAMPLE 6
TSK 3000 Gel Chromatography 200 ng of the sFv-huβ-Gluc fusion protein which had been purified by anti-idiotype affinity chromatography in 25 μl were chromatographed on a TSK gel G 3000 SW XL column (TOSO HAAS Order No. 3.5Wx N3211, 7.8 mm×300 mm) in a suitable mobile phase (PBS, pH 7.2, containing 5 g/l maltose and 4.2 g/l arginine) at a flow rate of 0.5 ml/ min. The Merck Hitachi HPLC system (L-4000 UV detector, L-6210 intelligent pump, D-2500 Chromato-integrator) was operated under ≈20 bar, the optical density of the eluate was determined at 280 nm, and an LKB 2111 Multisac fraction collector was used to collect 0.5 ml fractions which were subsequently analysed in a specificity enzyme activity test (SEAT) (EP 0 501 215 A2, Example J). The result of this experiment is shown in FIG. 1. It is clearly evident that the position of the peak detectable by measurement of the optical density at 280 nm coincides with the peak which determines the specificity and enzyme activity (SEAT) of the eluate. Based on the positions of the molecular weights of standard proteins which are indicated by arrows, it can be concluded that the functionally active sFv-huβ-Gluc fusion protein has an approximate molecular weight of ≈200 kDa under native conditions.

EXAMPLE 7
Workup of Organs/Tumors for Determination of the Fusion Protein

The following sequential steps were carried out:
- nude mice (CD1) which have a subcutaneous tumor and have been treated with fusion protein or antibody-enzyme conjugate undergo retroorbital exsanguination and are then sacrificed
- the blood is immediately placed in an Eppendorf tube which already contains 10 μl of Liquemin 25000 (from Hoffman-LaRoche AG)
- centrifugation is then carried out in a centrifuge (Megafuge 1.0, from Heraeus) at 2500 rpm for 10 min
- the plasma is then obtained and frozen until tested
- the organs or the tumor are removed and weighed
- they are then completely homogenized with 2 ml of 1% BSA in PBS, pH 7.2
- the tumor homogenates are adjusted to pH 4.2 with 0.1 N HCl (the sample must not be overtitrated because β-glucuronidase is inactivated at pH<3.8)
- all the homogenates are centrifuged at 16000 g for 30 min
- the clear supernatant is removed
- the tumor supernatants are neutralized with 0.1 N NaOH
- the supernatants and the plasma can now be quantified in immunological tests.

EXAMPLE 8
Triple Determinant Test

The tests are carried out as follows:
- 75 μl of a mouse anti-huβ-Gluc antibody (MAb 2118/157 Behringwerke) diluted to 2 μg/ml in PBS, pH 7.2, are placed in each well of a microtiter plate (polystyrene U-shape, type B, from Nunc, Order No. 4-60445)
- the microtiter plates are covered and incubated at R.T. overnight
- the microtiter plates are subsequently washed 3× with 250 μl of 0.05 M tris-citrate buffer, pH 7.4, per well
- these microtiter plates coated in this way are incubated with 250 μl of blocking solution (1% casein in PBS, pH 7.2) in each well at R.T. for 30' (blocking of non-specific binding sites) (coated microtiter plates which are not required are dried at R.T. for 24 hours and then sealed together with drying cartridges in coated aluminum bags for long-term storage)
- during the blocking, in an untreated 96-well U-shaped microtiter plate (polystyrene, from Renner, Order No. 12058), 10 samples+2 positive controls+1 negative control are diluted 1:2 in 1% casein in PBS, pH 7.2, in 8 stages (starting from 150 μl of sample, 75 μl of sample are pipetted into 75 μl of casein solution etc.)
- the blocking solution is aspirated out of the microtiter plate coated with anti-huβ-Gluc anti-bodies, and 50 μl of the diluted samples are transferred per well from the dilution plate to the test plate and incubated at R.T. for 30 min
- during the sample incubation, the ABC-AP reagent (from Vectastain, Order No. AK-5000) is made up: thoroughly mix 2 drops of reagent A (Avidin DH) in 10 ml of 1% casein in PBS, pH 7.2, add 2 drops of reagent B (biotinylated alkaline phosphatase) add mix thoroughly. (The ABC-AP solution must be made up at least 30' before use.)
- the test plate is washed 3 times with ELISA washing buffer (Behringwerke, Order No. OSEW 96)
- 50 μl of biotin-labeled detecting antibody mixture (1+1 mixture of mouse anti 431/26 antibody (MAb 2064/353, Behringwerke) and mouse anti-CEA antibody (MAb 250/183, Behringwerke) in a concentration of 5 μg/ml diluted in 1% casein in PBS, pH 7.2, final concentration of each antibody of 2.5 μg/ml) are placed in each well
- the test plate is washed 3 times with ELISA washing buffer 50 µl of the prepared ABC-AP solution are placed in each well and incubated at R.T. for 30 min during the ABC-AP incubation, the substrate is made up (fresh substrate for each test: 1 mM 4-methylumbelliferyl phosphate, Order No. M-8883, from Sigma, in 0.5 M tris +0.01% MgCl$_2$, pH 9.6)

the test plate is washed 7 times with ELISA washing buffer

50 µl of substrate are loaded into each well, and the test plate is covered and incubated at 37° C. for 2 h 150 µl of stop solution (0.2 M glycine+0.2% SDS, pH 11.7) are subsequently added to each well the fluorometric evaluation is carried out in a Fluoroscan II (ICN Biomedicals, Cat.No. 78-611-00) with an excitation wavelength of 355 nm and an emission wavelength of 460 nm the unknown concentration of fusion protein in the sample is determined on the basis of the fluorescence values for the positive control included in the identical experiment (dilution series with purified sFv-huβ-Gluc mixed with CEA 5 µg/ml as calibration plot).

EXAMPLE 9

Expression of the sFv-huβ-Gluc Fusion Protein in Yeast.

Figure 9:
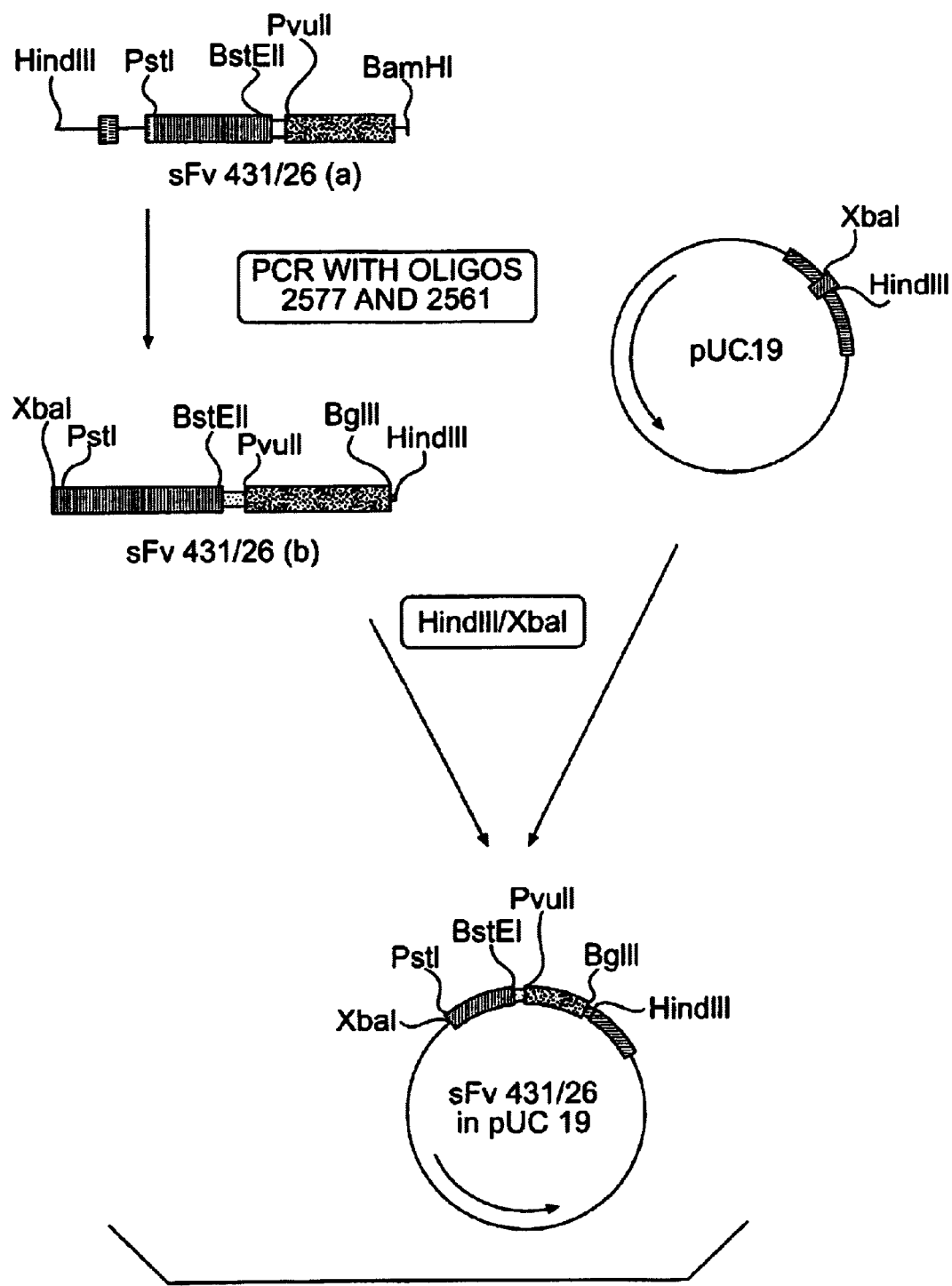
FIG. 9 is a schematic representation of the amplification of the single-chain Fv, sFv 431/26, by PCR using oligonucleotides 2561 and 2577, and the cloning of that single-chain Fv into the vector pUC19.

The single-chain Fv (sFv) from Example 2 is amplified with the oligos 2577 (SEQ ID NO:8) and 2561 (SEQ ID NO:7) (FIG. 2) and cloned into the vector pUC19 which has been digested with XbaI/HindIII (FIG. 9).

Figure 10:
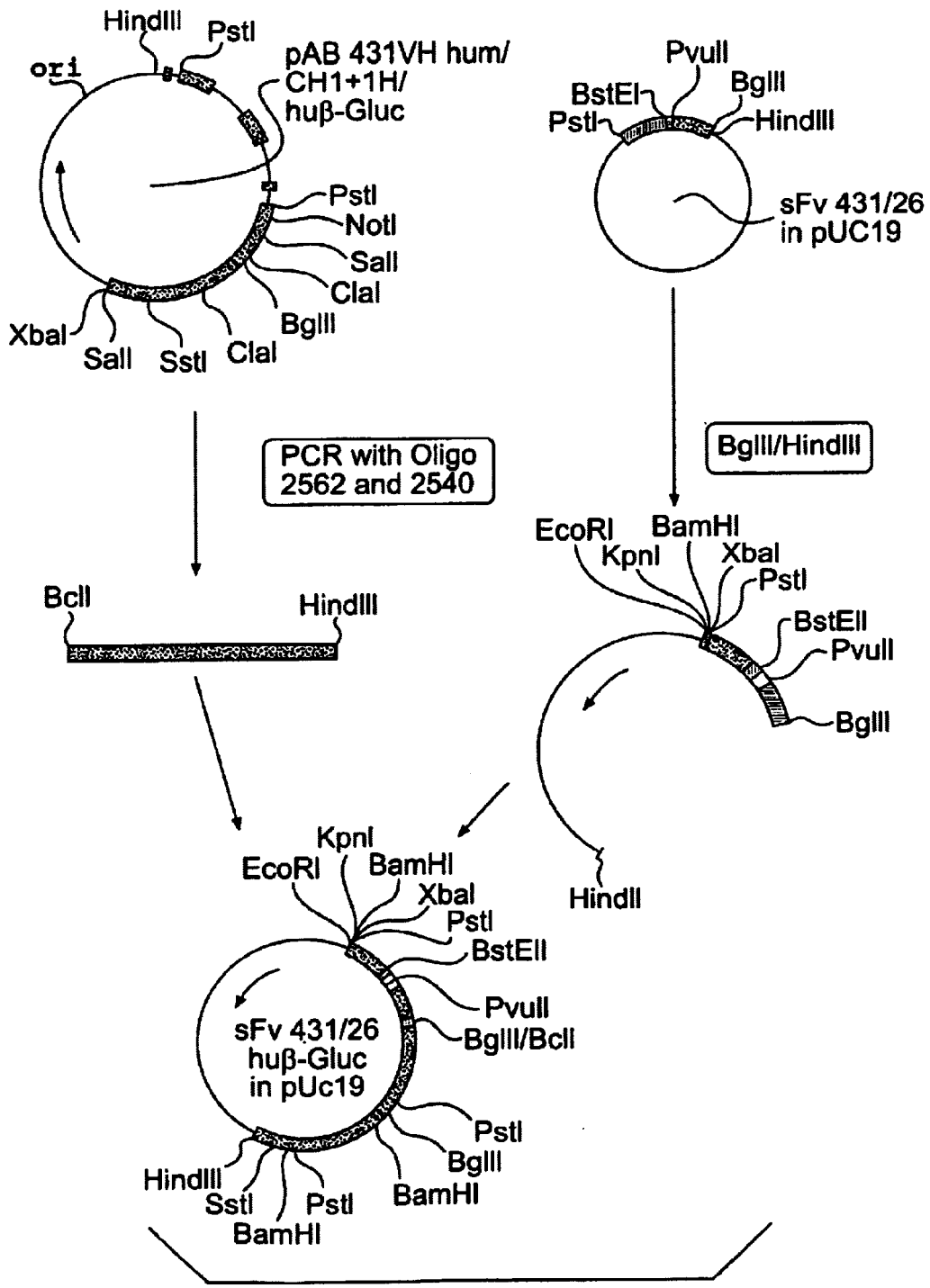
FIG. 10 is a schematic representation of the amplification of the human β-glucuronidase gene from the plasmid pAB 431$V_H$ hum/CH1+1H/huβ-Gluc by PCR using oligonucleotides 2562 and 2540, and the ligation of that gene into the plasmid sFv 431/26 in pUC19.

The human β-glucuronidase gene is amplified with the oligos 2562 (SEQ ID NO:9) and 2540 (SEQ ID NO:10) (FIG. 8) from the plasmid pAB 431/26 V$_H$hum/CH1+1H/β-Gluc (Example 3) and ligated into the plasmid sFv 431/26 in pUC19 (FIG. 9) cut with BglII/HindIII (FIG. 10).

Figure 11:
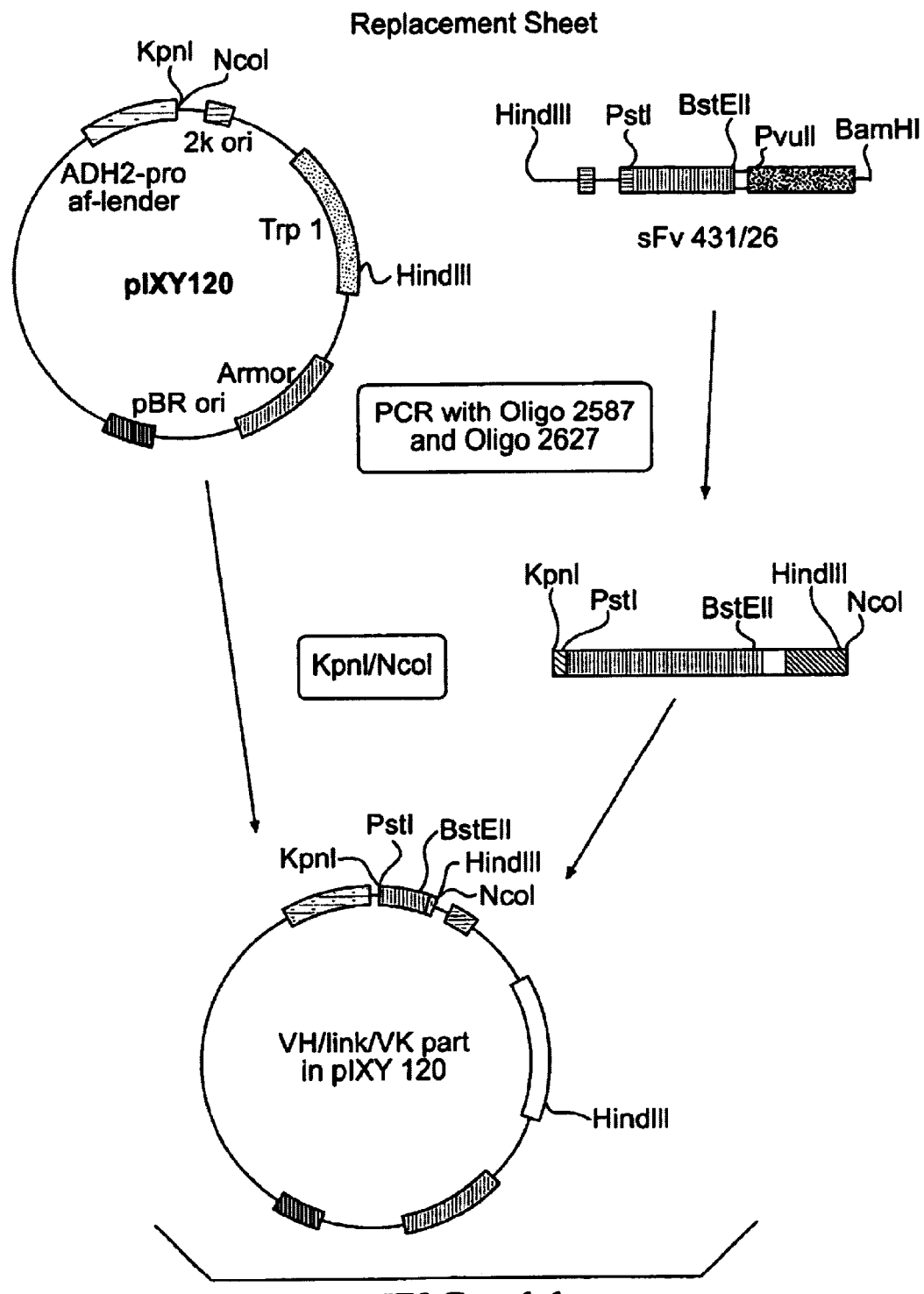
FIG. 11 is a schematic representation of the amplification of a KpnI/NcoI fragment from the sFv 431/26 by PCR using oligonucleotides 2587 and 2627, and the cloning of that fragment into the yeast expression vector pIXY.

A KpnI/NcoI fragment is amplified with the oligos 2587 (SEQ ID NO:11) and 2627 (SEQ ID NO:12) (FIG. 8) from the sFv 431/26 and cloned into the yeast expression vector pIXY digested with KpnI/NcoI (FIG. 11).

Figure 12:
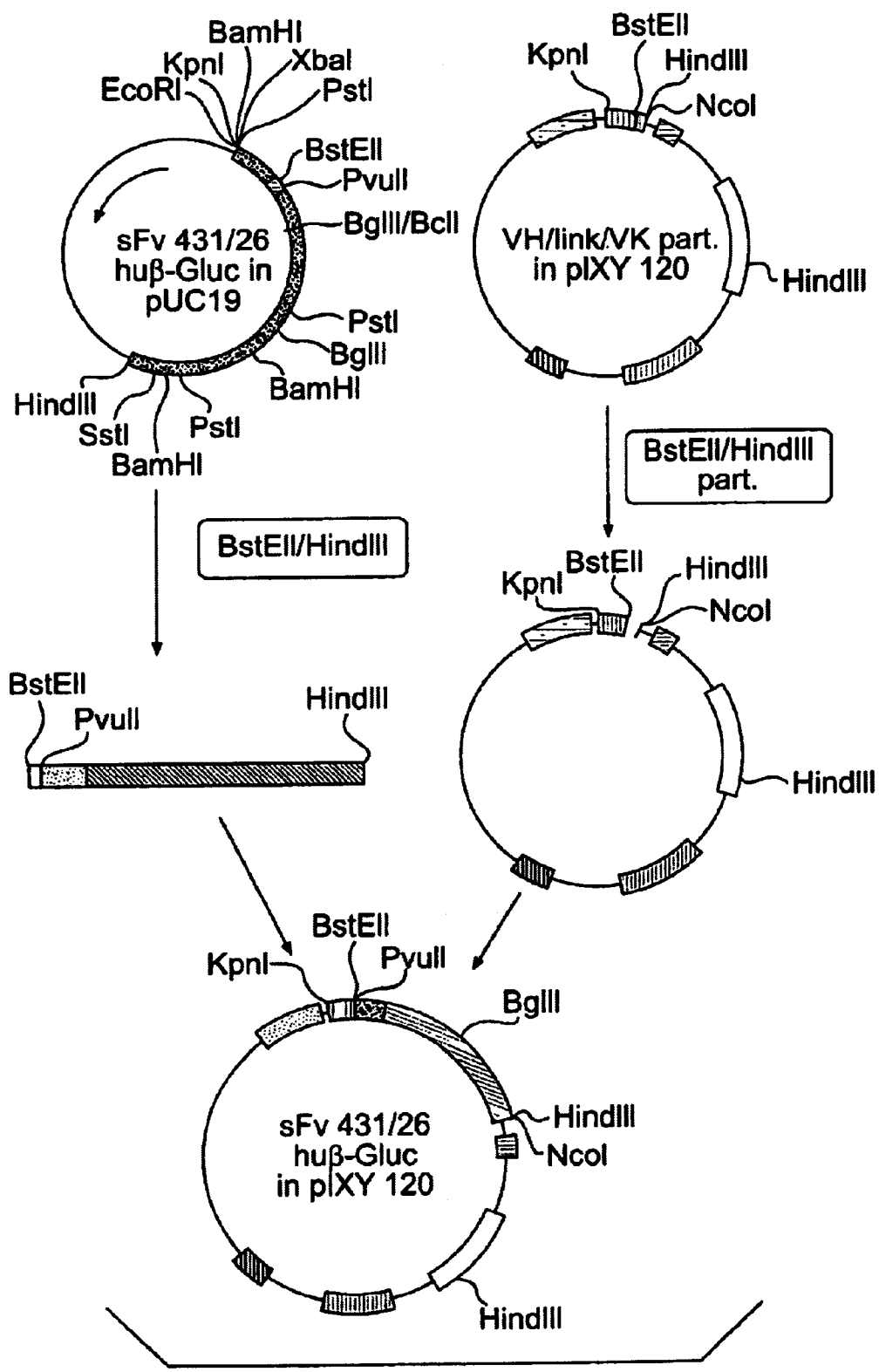
FIG. 12 is a schematic representation of the ligation the BstEII/HindIII fragment from the plasmid sFv 431/26 huβ-Gluc in pUC19 into the vector pIXY 120 containing a $V_H$ gene, a linker, and a part of a $V_L$ gene.

The BstEII/HindIII fragment from the plasmid sFv 431/26 huβ-Gluc in pUC19 (FIG. 10) is ligated into the vector pIXY 120 which harbors the V$_H$ gene, the linker and a part of the V$_L$ gene (V$_H$/link/V$_K$ part. in pIXY 120) and has been digested with BstEII/partially with HindIII (FIG. 12).

The resulting plasmid sFv 431/26 huβ-Gluc in pIXY 120 is transformed into *Saccharomyces cerevisiae* and the fusion protein is expressed.

EXAMPLE 10

Expression of the sFv-*E.coli*-β-glucuronidase Fusion Protein in Yeast.

Figure 14:
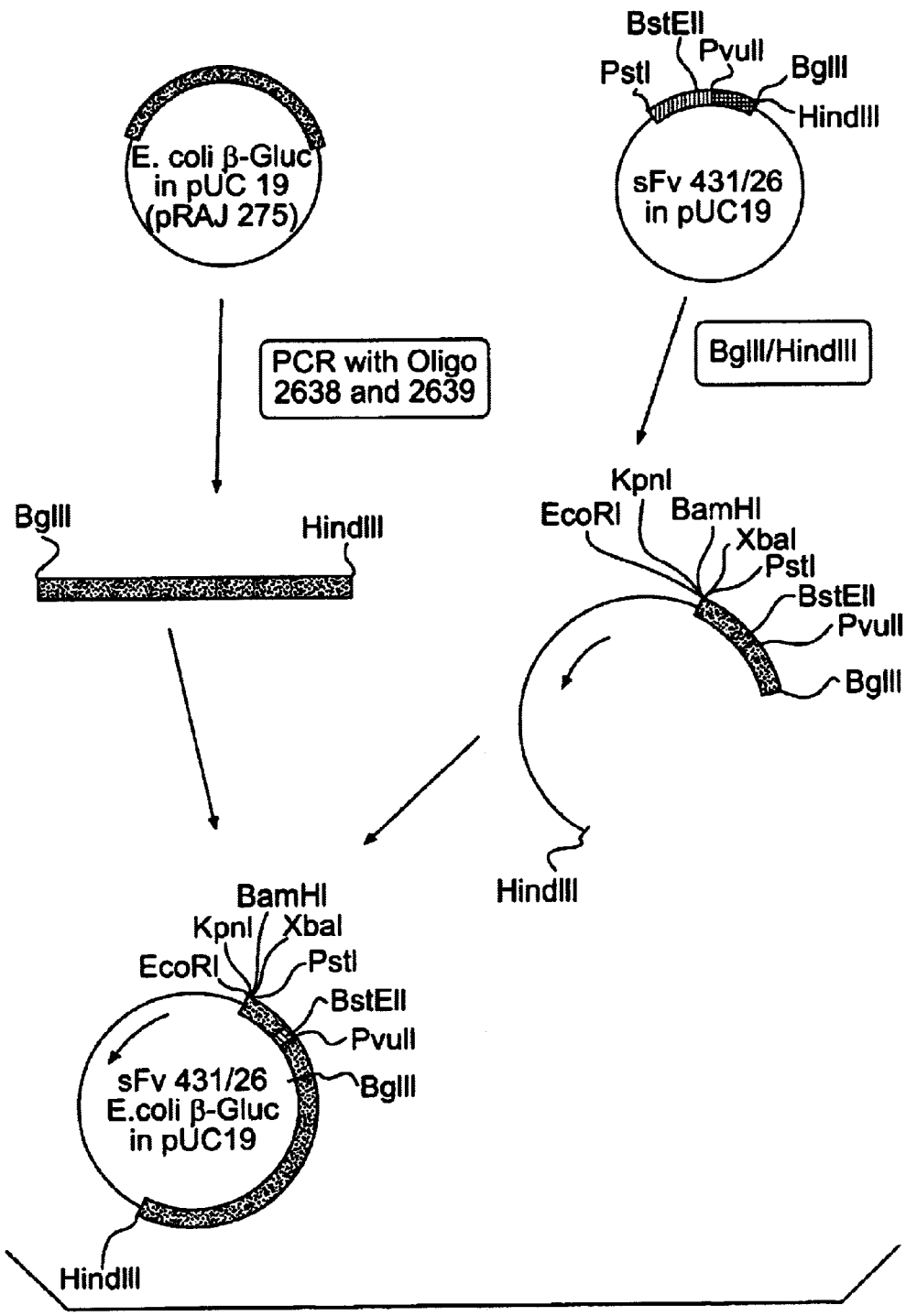
FIG. 14 is a schematic representation of the amplification of the E. coli glucuronidase gene from the plasmid pRAJ275 by PCR using oligonucleotides 2638 and 2639, and the ligation of that gene into sFv 431/26 in pUC19.

The *E.coli* glucuronidase gene is amplified from pRAJ 275 (Jefferson et al. Proc. Natl. Acad. Sci, USA, 83: 8447–8451, 1986) with the oligos 2638 (SEQ ID NO:14) and 2639 (SEQ ID NO:13) (FIG. 13) and ligated into sFv 431/26 in pUC19 (Example 9, FIG. 9) cut with BglII/HindIII (FIG. 14).

Figure 15:
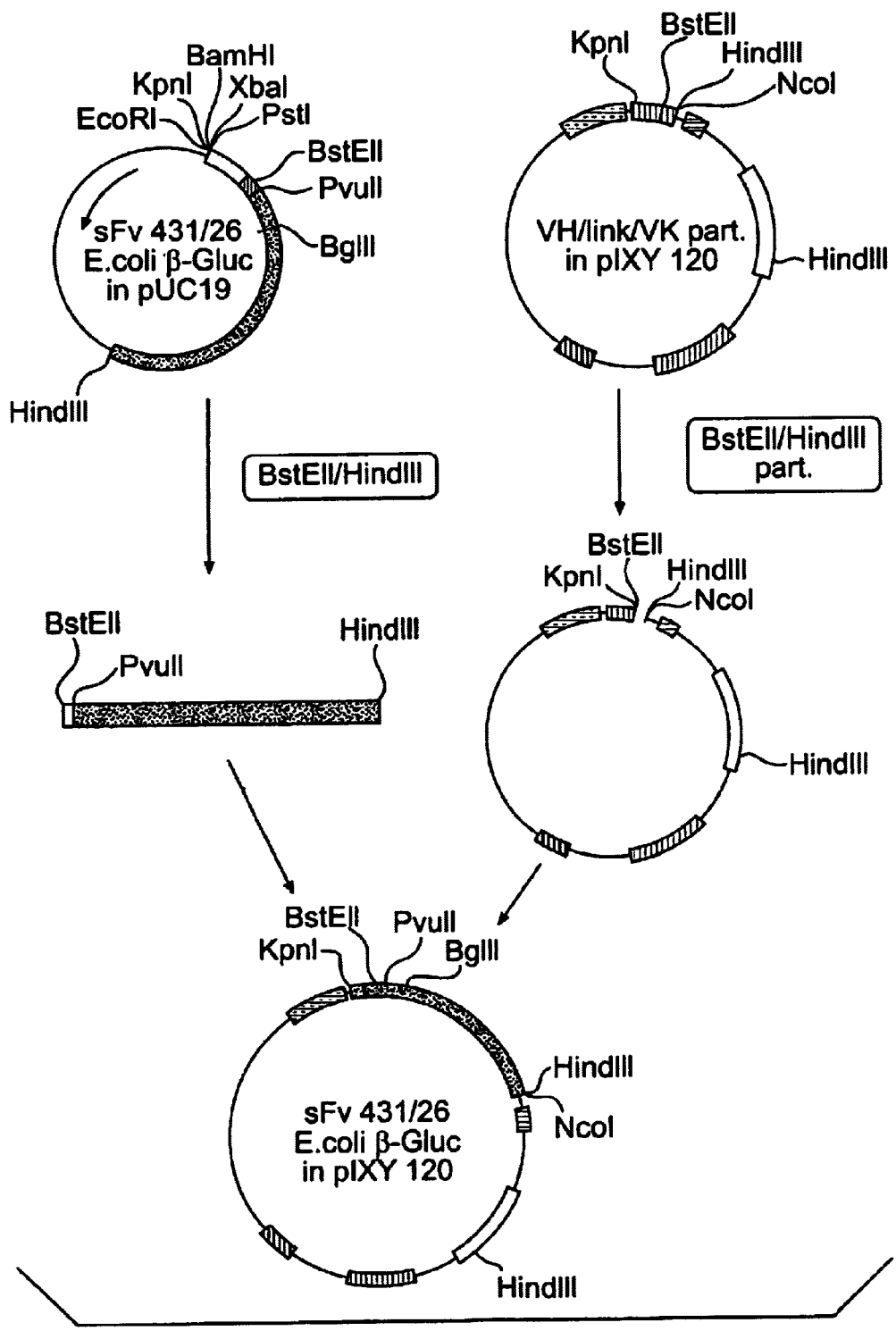
FIG. 15 is a schematic representation of the cloning of the BstEII/HindIII fragment from the plasmid sFv 431/26 E. coli β-Gluc in pUC19 into the vector pIXY 120.

A BstEII/HindIII fragment from sFv 431/26 *E.coli* β-Gluc in pUC19 is cloned into the vector V$_H$/link/V$_K$ part in pIXY 120 (Example 9, FIG. 11) which has been partially digested with BstEII/HindIII (FIG. 15).

The plasmid sFv 431/26 *E.coli* β-Gluc in pIXY 120 is transformed into *Saccharomyces cerevisiae* and the fusion protein is expressed.

EXAMPLE 11

Expression of the sFv-β-lactamase Fusion Protein in Yeast.

Figure 17:
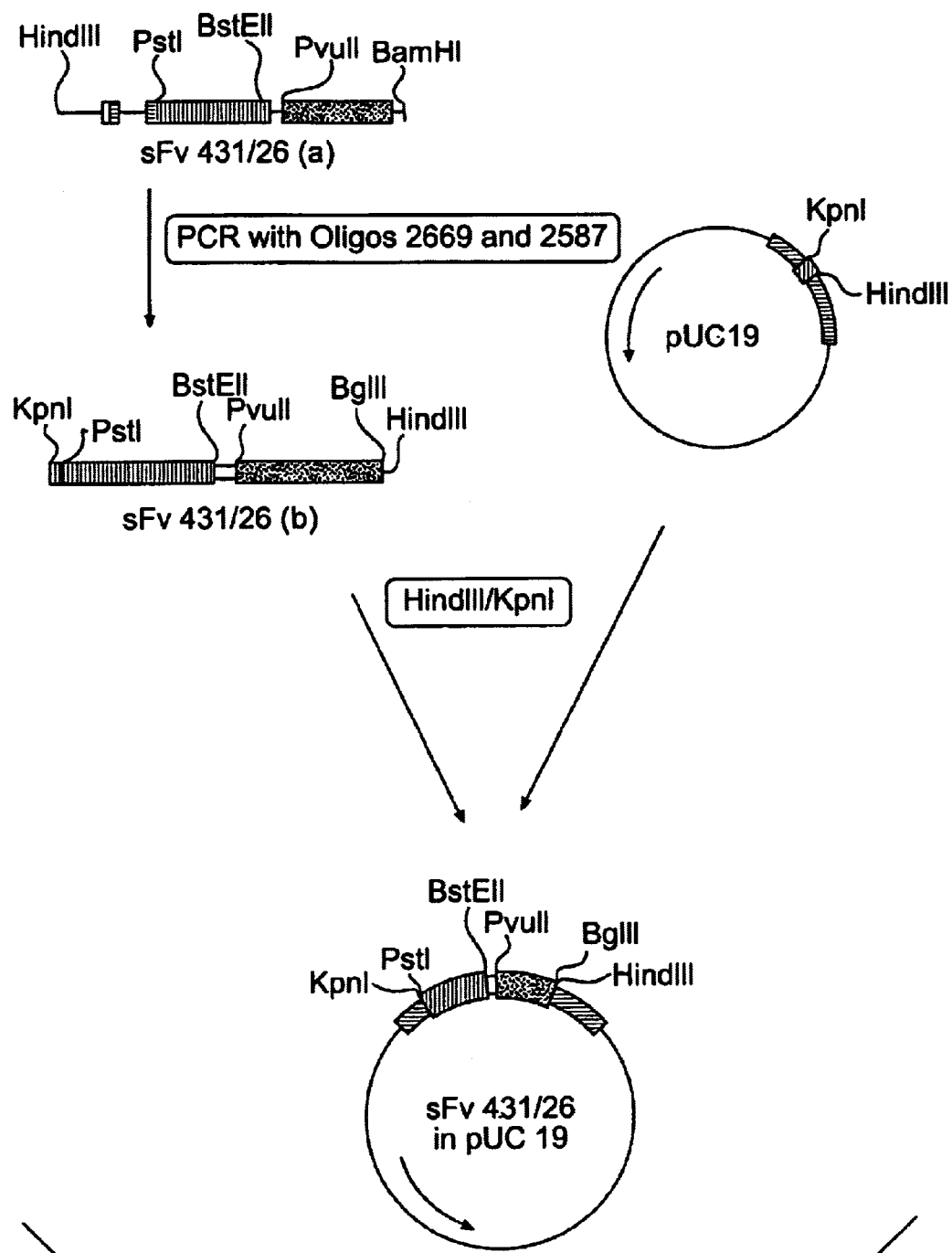
FIG. 17 is a schematic representation of the amplification of sFv 431/26 by PCR using oligonucleotides 2587 and 2669, and the cloning of sFv 431/26 into the vector pUC19.

The single-chain Fv (sFv) from Example 2 is amplified with the oligos 2587 (SEQ ID NO:15) and 2669 (SEQ ID NO:16) (FIG. 16) and ligated into the pUC19 vector digested with KpnI/HindIII (FIG. 17).

Figure 18:
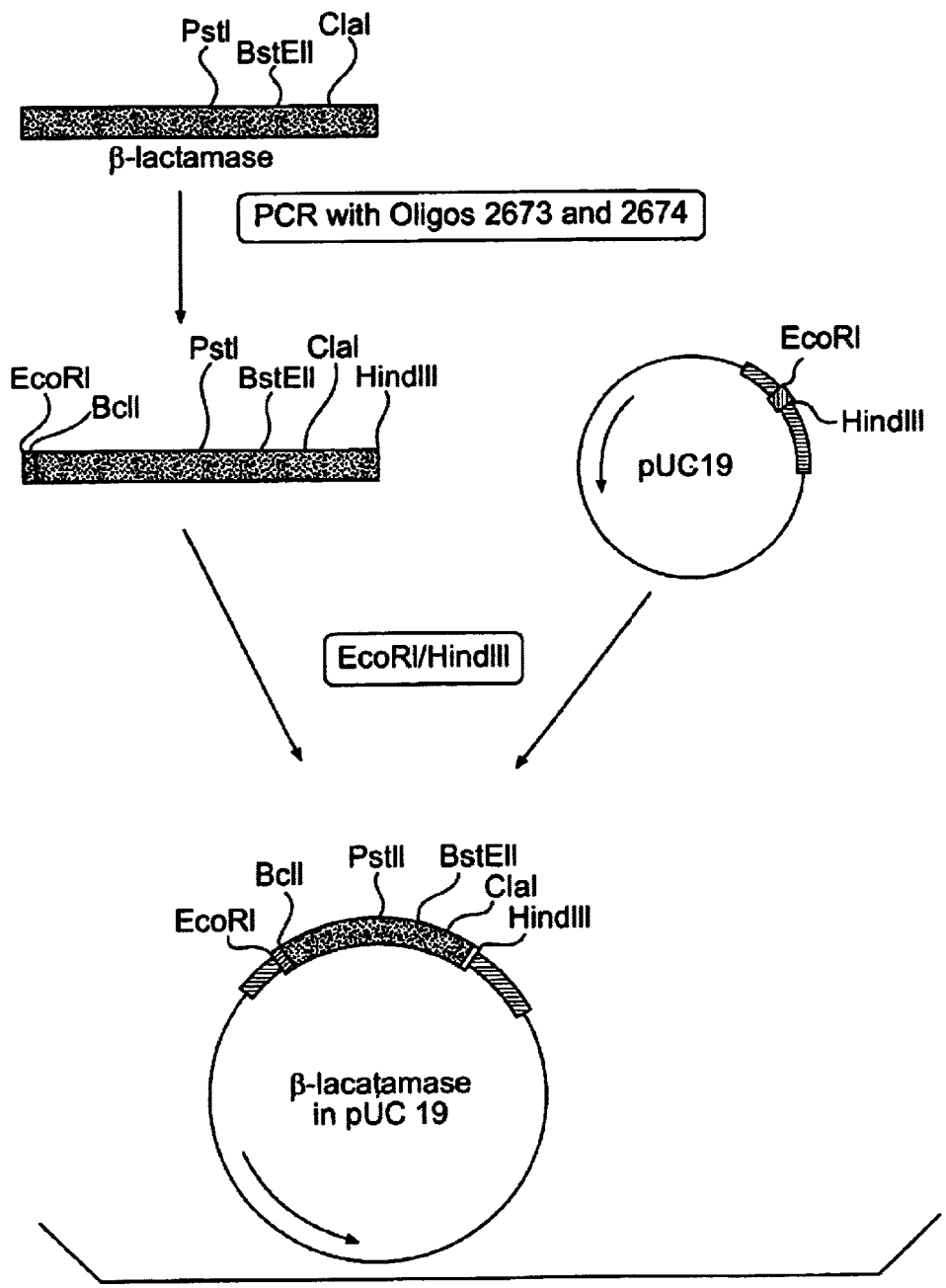
FIG. 18 is a schematic representation of the amplification of the β-lactamase II gene from the complete DNA of *Bacillus cereus* by PCR using oligonucleotides 2673 and 2674, and the cloning of that gene into the vector pUC19.
Figure 19:
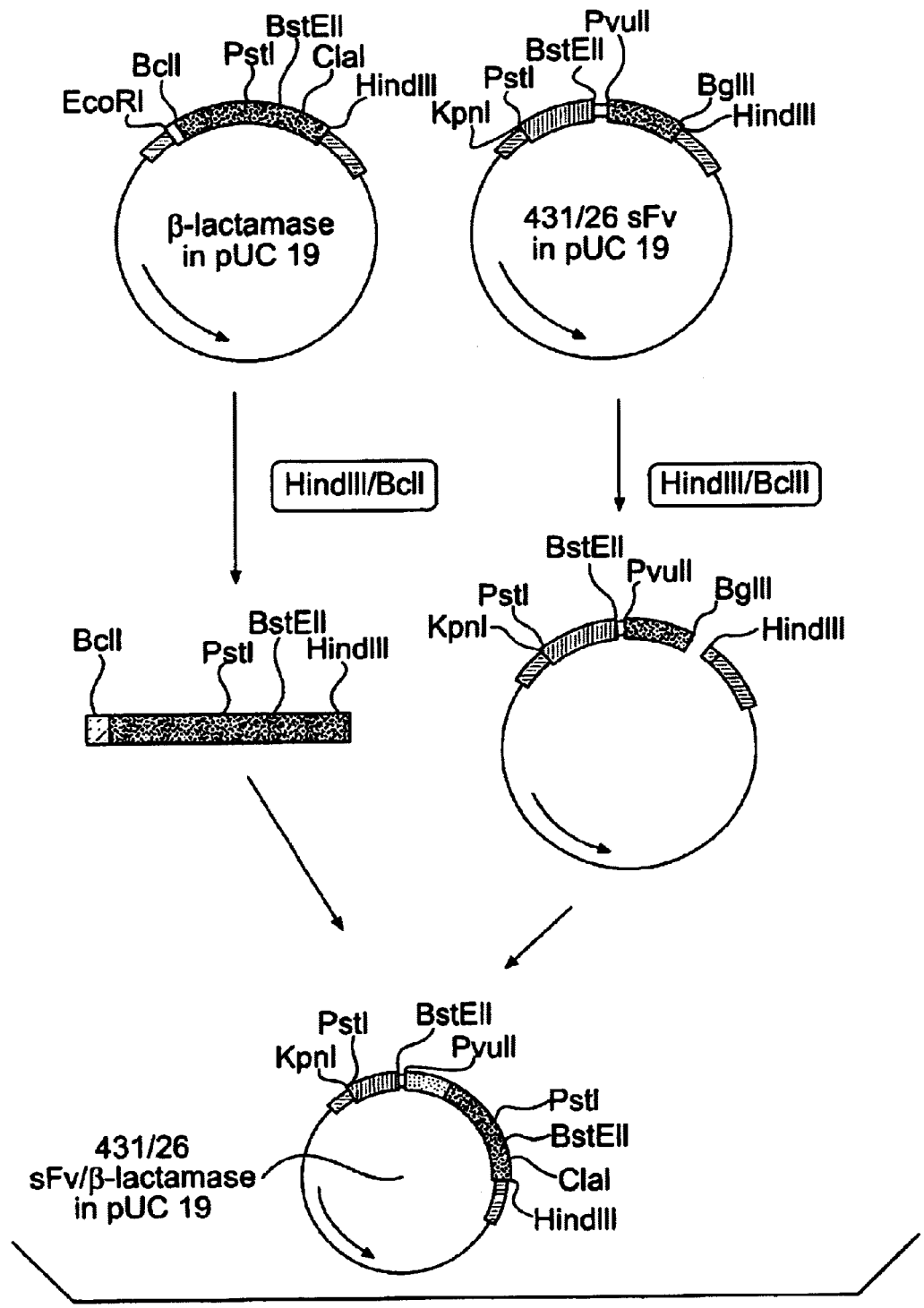
FIG. 19 is a schematic representation of the ligation of a BclI/HindIII fragment of the β-lactamase gene into sFv 431/26 in pUC19.

The β-lactamase II gene (Hussain et al., J. Bacteriol. 164: 223–229, 1985) is amplified with the oligos 2673 (SEQ ID NO:17) and 2674 (SEQ ID NO:18) (FIG. 16) from the complete DNA of *Bacillus cereus* and ligated into the pUC19 vector digested with EcoRI/HindIII (FIG. 18). A BclI/HindIII fragment of the β-lactamase gene is ligated into sFv 431/26 in pUC19 which has been cut with BglII/HindIII (FIG. 17).

Figure 20:
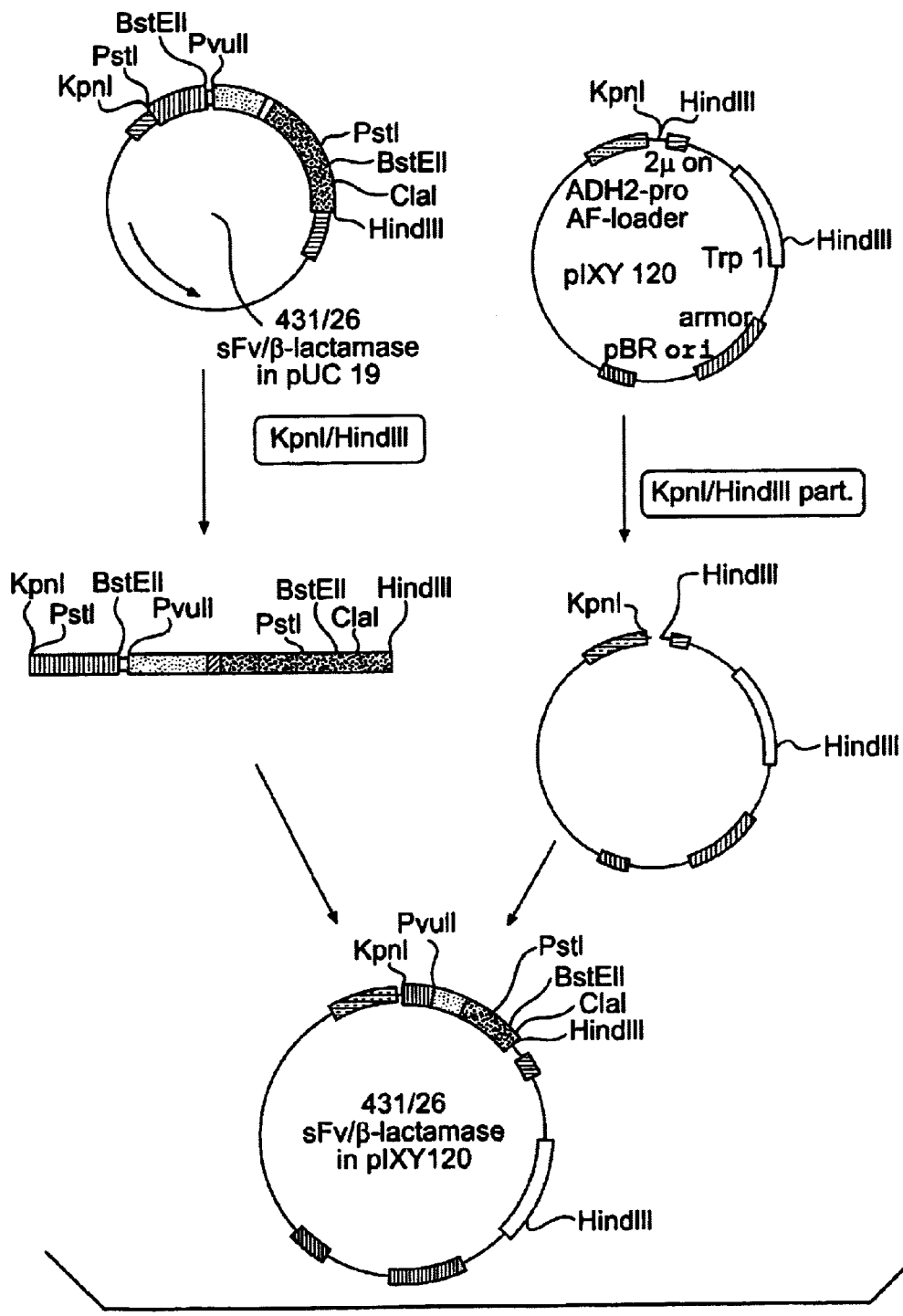
FIG. 20 is a schematic representation of the ligation of the KpnI/HindIII sFv β-lactamase fragment into the vector pIXY 120.

The KpnI/HindIII sFv-β-lactamase fragment is ligated into pIXY 120 which has been digested with KpnI/partially with HindIII (FIG. 20). The plasmid is transformed into *Saccharomyces cerevisiae*, and a fusion protein which has both the antigen-binding properties of MAb 431/26 and the enzymatic activity of *Bacillus cereus* β-lactamase is expressed.

TABLE 1

Pharmacokinetics of sFv-hu β Gluc fusion protein in CD1 nu/nu mice carrying MzSto1 ng of sFv-huβGluc per gram of tissue or ml of plasma measured in the triple determinant test

| Tissue type | Mouse 1 0.05 h | Mouse 2 3 h | Mouse 3 24 h | Mouse 4 48 h | Mouse 5a 120 h | Mouse 5b 120 h |
|---|---|---|---|---|---|---|
| Tumor | 24.8 | 4 | 7.7 | 2.1 | 2.2 | 6.2 |
| Spleen | 15.4 | 4.1 | <0.1 | <0.1 | <0.1 | <0.1 |
| Liver | 40.9 | 10.1 | 0.8 | 0.8 | 0.3 | <0.1 |
| Intestine | 5.2 | 4.4 | 1.1 | 1.2 | 0.6 | <0.1 |
| Kidney | 44.4 | 7 | <0.1 | <0.1 | <0.1 | <0.1 |
| Lung | 154.8 | 17.3 | <0.1 | <0.1 | <0.1 | <0.1 |
| Heart | 148.3 | 8.2 | <0.1 | <0.1 | <0.1 | <0.1 |
| Plasma | 630.9 | 95 | 2.7 | 0.4 | <0.1 | <0.1 | i.v. injection of 0.8 µg of purified fusion protein per mouse

TABLE 2

Analysis of the monosaccharide components in the carbohydrate content of the sFv-huβ-Gluc fusion protein from BHK cells The purified sFv-huβ-Gluc fusion protein was investigated for its carbohydrate content. This revealed after hydrolysis the following individual components in the stated molar ratio (mol of carbohydrate/mol of sFv-huβ-Gluc).

|  | Fucose | Galactosamine | N-Acetyl-glucosamine | Galactose | Glucose | Mannose | N-Acetyl-neuraminic acid |
|---|---|---|---|---|---|---|---|
| sFv-huβ-Gluc | 4 | 2 | 30 | 8 | 1 | 43 | 4 |

TABLE 3

Analysis of the monosaccharide components in the carbohydrate content of the sFv-huβGluc fusion protein from *Saccharomyces cerevisiae*.

|  | Glucosamine | Glucose | Mannose |  |
|---|---|---|---|---|
| sFv-huβGluc (mol/mol) | 6 | 12 | 150 | mol/mol |

---

What is claimed is:

1. A compound comprising two or more antigen binding regions linked to at least one prodrug-activating enzyme, wherein
   a) the antigen binding region consists of a single polypeptide chain;
   b) the single polypeptide chain is comprised of a first variable domain, a second variable domain, and a polypeptide linker connecting the first variable domain and the second variable domain, wherein a nucleotide sequence encoding the polypeptide linker is formed by two partially overlapping PCR primers during aPCR reaction that links the first variable domain and the second variable domain;
   c) the compound has a bivalent or a multivalent structure; and wherein
   d) the compound is glycosylated.

2. A compound as claimed in claim 1, wherein at least one antigen binding region comprises a variable domain of a heavy antibody chain and a variable domain of a light antibody chain (sFv fragment).

3. A compound as claimed in claim 2, wherein the TAA is selected from the group consisting of an N-CAM, PEM, EGF-R, Sialyl-Le, Sialyl-Le$^x$, TFβ, GICA, GD$_3$, GD$_2$, TAG72, CA125, the 24–25 kDa glycoprotein defined by MAb 6, and CEA.

4. A compound as claimed in claim 1, wherein at least one of the antigen binding regions binds to a tumor-associated antigen (TAA).

5. A compound as claimed in claim 1, wherein the enzyme is selected from the group consisting of a lactamase, pyroglutamate aminopeptidase, D-aminopeptidase, oxidase, peroxidase, phosphatase, hydroxynitrile lyase, protease, esterase, carboxypeptidase, and glycosidase.

6. A compound as claimed in claim 5, wherein the enzyme is a β-glucuronidase, which is selected from the group consisting of an *E. coli* β-glucuronidase, a *Kobayasia nipponica* β-glucuronidase, a *Secale cereale* β-glucuroniciase and a human β-glucuronidase.

7. A compound as claimed in claim 5, wherein the lactamase enzyme is a *Bacillys cereus* β-lactamase II.

8. A compound as claimed in claim 5, wherein the carboxypeptidase enzyme is a carboxypeptidase G2 from *Pseudomonas*.

9. A compound as claimed in claim 1, wherein at least one of the antigen binding regions is linked to the enzyme via a peptide linker.

10. A compound as claimed in claim 1, wherein glycosylation covalently bonds the carbohydrates to the compound, and the glycosylation takes place by means of chemical methods.

11. A compound as claimed in claim 1, wherein glycosylation covatently bonds carbohydrates to the compound, and the glycosylation takes place by a selection of suitable expression systems.

12. A compound as claimed in claim 1, which has undergone secretory expression in *Saccharomyces cerevisiae* or in *Hansenula polymorpha*.

13. A compound as claimed in claim 12, which has undergone secretory expression in *Hansenula polymorpha*.

14. A compound as claimed in claim 1, which is expressed in *E. coli* and is subsequentty chemically glycosylated.

15. A compound as claimed in claim 14, wherein the chemical glycosylation involves at least one of galactosylation or mannosylation.

16. A pharmaceutical containing a compound as claimed in claim 1 and a physiologically acceptable carrier.

17. A diagnostic aid comprising a compound as claimed in claim 1.

18. A compound as claimed in claim 1, wherein the antigen binding regions and the at least one prodrug-activating enzyme form an sFv-β-lactamase fusion protein.

19. A compound as claimed in claim 18, wherein the sFv β-lactamase fusion protein has undergone periplasmic expression in *E coli*, and is subsequently chemically glycosylated.

20. A compound as claimed in claim 19, wherein the chemical glycosylation involves at least one of galactosylation or mannosylation.

21. A compound as claimed in claim 18, wherein the sFv β-lactamase fusion protein has undergone secretory expression in *Saccharomyces cerevisiae* or *Hansenula polymorpha*.

22. A method of treating cancer comprising administering a compound claimed in claim 1 to a host in need thereof and subsequently administering a prodrug to be activated by the enzyme portion of the compound of claim 1.

23. A compound comprising one or more antigen binding regions linked to at least one prodrug-activating enzyme, wherein
 a) the antigen binding regions consist of a single polypeptide chain;
 b) the single polypeptide chain is comprised of a first variable domain, a second variable domain, and a polypeptide linker connecting the first variable domain and the second variable domain, wherein a nucleotide sequence encoding the polypeptide linker is formed by two partially overlapping PCR primers during a PCR reaction that links the first variable domain and the second variable domain;
 c) the compound has a monovalent, bivalent, or multivalent structure; and wherein
 d) the compound is glycosylated.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 3314 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: sig_peptide
        (B) LOCATION: 145..283

(ix) FEATURE:
        (A) NAME/KEY: mat_peptide
        (B) LOCATION: join(284..1003, 1069..1119, 1263..3161)

(ix) FEATURE:
        (A) NAME/KEY: CDS
        (B) LOCATION: join(145..189, 272..1003, 1069..1119, 1263..3161)

(xi) SEQUENCE DESCRIPTION: SEQ ID NO: 1:

```
CCAAGCTTAT GAATATGCAA ATCCTGCTCA TGAATATGCA AATCCTCTGA ATCTACATGG        60

TAAATATAGG TTTGTCTATA CCACAAACAG AAAAACATGA GATCACAGTT CTCTCTACAG       120

TTACTGAGCA CACAGGACCT CACC ATG GGA TGG AGC TGT ATC ATC CTC TTC         171
                          Met Gly Trp Ser Cys Ile Ile Leu Phe
                          -19                 -15

TTG GTA GCA ACA GCT ACA GGTAAGGGGC TCACAGTAGC AGGCTTGAGG                219
Leu Val Ala Thr Ala Thr
-10              -5

TCTGGACATA TATATGGGTG ACAATGACAT CCACTTTGCC TTTCTCTCCA CA GGT           274
```

|  |  |
|---|---|
|                                Gly<br>                               -4 |  |
| GTC CAC TCC CAG GTC CAA CTG CAG GAG AGC GGT CCA GGT CTT GTG AGA<br>Val His Ser Gln Val Gln Leu Gln Glu Ser Gly Pro Gly Leu Val Arg<br>            1                   5                 10 | 322 |
| CCT AGC CAG ACC CTG AGC CTG ACC TGC ACC GTG TCT GGC TTC ACC ATC<br>Pro Ser Gln Thr Leu Ser Leu Thr Cys Thr Val Ser Gly Phe Thr Ile<br>      15                  20                25 | 370 |
| AGC AGT GGT TAT AGC TGG CAC TGG GTG AGA CAG CCA CCT GGA CGA GGT<br>Ser Ser Gly Tyr Ser Trp His Trp Val Arg Gln Pro Pro Gly Arg Gly<br>30                  35                40                45 | 418 |
| CTT GAG TGG ATT GGA TAC ATA CAG TAC AGT GGT ATC ACT AAC TAC AAC<br>Leu Glu Trp Ile Gly Tyr Ile Gln Tyr Ser Gly Ile Thr Asn Tyr Asn<br>                50                55              60 | 466 |
| CCC TCT CTC AAA AGT AGA GTG ACA ATG CTG GTA GAC ACC AGC AAG AAC<br>Pro Ser Leu Lys Ser Arg Val Thr Met Leu Val Asp Thr Ser Lys Asn<br>      65                  70                75 | 514 |
| CAG TTC AGC CTG AGA CTC AGC AGC GTG ACA GCC GCC GAC ACC GCG GTC<br>Gln Phe Ser Leu Arg Leu Ser Ser Val Thr Ala Ala Asp Thr Ala Val<br>          80                  85              90 | 562 |
| TAT TAT TGT GCA AGA GAA GAC TAT GAT TAC CAC TGG TAC TTC GAT GTC<br>Tyr Tyr Cys Ala Arg Glu Asp Tyr Asp Tyr His Trp Tyr Phe Asp Val<br>          95                 100             105 | 610 |
| TGG GGC CAA GGG ACC ACG GTC ACC GTC TCC TCA GGA GGC GGT GGA TCG<br>Trp Gly Gln Gly Thr Thr Val Thr Val Ser Ser Gly Gly Gly Gly Ser<br>110               115               120              125 | 658 |
| GGC GGT GGT GGG TCG GGT GGC GGC GGA TCT GAC ATC CAG CTG ACC CAG<br>Gly Gly Gly Gly Ser Gly Gly Gly Gly Ser Asp Ile Gln Leu Thr Gln<br>                130               135              140 | 706 |
| AGC CCA AGC AGC CTG AGC GCC AGC GTG GGT GAC AGA GTG ACC ATC ACC<br>Ser Pro Ser Ser Leu Ser Ala Ser Val Gly Asp Arg Val Thr Ile Thr<br>          145                150              155 | 754 |
| TGT AGT ACC AGC TCG AGT GTA AGT TAC ATG CAC TGG TAC CAG CAG AAG<br>Cys Ser Thr Ser Ser Ser Val Ser Tyr Met His Trp Tyr Gln Gln Lys<br>                160               165              170 | 802 |
| CCA GGT AAG GCT CCA AAG CTG CTG ATC TAC AGC ACA TCC AAC CTG GCT<br>Pro Gly Lys Ala Pro Lys Leu Leu Ile Tyr Ser Thr Ser Asn Leu Ala<br>175               180               185 | 850 |
| TCT GGT GTG CCA AGC AGA TTC AGC GGT AGC GGT AGC GGT ACC GAC TTC<br>Ser Gly Val Pro Ser Arg Phe Ser Gly Ser Gly Ser Gly Thr Asp Phe<br>190               195              200              205 | 898 |
| ACC TTC ACC ATC AGC AGC CTC CAG CCA GAG GAC ATC GCC ACC TAC TAC<br>Thr Phe Thr Ile Ser Ser Leu Gln Pro Glu Asp Ile Ala Thr Tyr Tyr<br>                210               215              220 | 946 |
| TGC CAT CAG TGG AGT AGT TAT CCC ACG TTC GGC CAA GGG ACC AAG CTG<br>Cys His Gln Trp Ser Ser Tyr Pro Thr Phe Gly Gln Gly Thr Lys Leu<br>          225                230              235 | 994 |
| GAG ATC AAA GGTGAGTAGA ATTTAAACTT TGCTTCCTCA GTTGGATCTG<br>Glu Ile Lys<br>          240 | 1043 |
| AGTAACTCCC AATCTTCTCT CTGCA GAG CTC AAA ACC CCA CTT GGT GAC ACA<br>                                    Glu Leu Lys Thr Pro Leu Gly Asp Thr<br>                                                                 245 | 1095 |
| ACT CAC ACA TGC CCA CGG TGC CCA GGTAAGCCAG CCCAGGACTC GCCCTCCAGC<br>Thr His Thr Cys Pro Arg Cys Pro<br>250               255 | 1149 |
| TCAAGGCGGG ACAAGAGCCC TAGAGTGGCC TGAGTCCAGG GACAGGCCCC AGCAGGGTGC | 1209 |
| TGACGCATCC ACCTCCATCC CAGATCCCCG TAACTCCCAA TCTTCTCTCT GCA GCG<br>                                                                                   Ala | 1265 |

```
GCG GCG GCG GTG CAG GGC GGG ATG CTG TAC CCC CAG GAG AGC CCG TCG        1313
Ala Ala Ala Val Gln Gly Gly Met Leu Tyr Pro Gln Glu Ser Pro Ser
        260                 265                 270

CGG GAG TGC AAG GAG CTG GAC GGC CTC TGG AGC TTC CGC GCC GAC TTC        1361
Arg Glu Cys Lys Glu Leu Asp Gly Leu Trp Ser Phe Arg Ala Asp Phe
275                 280                 285                 290

TCT GAC AAC CGA CGC CGG GGC TTC GAG GAG CAG TGG TAC CGG CGG CCG        1409
Ser Asp Asn Arg Arg Arg Gly Phe Glu Glu Gln Trp Tyr Arg Arg Pro
                    295                 300                 305

CTG TGG GAG TCA GGC CCC ACC GTG GAC ATG CCA GTT CCC TCC AGC TTC        1457
Leu Trp Glu Ser Gly Pro Thr Val Asp Met Pro Val Pro Ser Ser Phe
            310                 315                 320

AAT GAC ATC AGC CAG GAC TGG CGT CTG CGG CAT TTT GTC GGC TGG GTG        1505
Asn Asp Ile Ser Gln Asp Trp Arg Leu Arg His Phe Val Gly Trp Val
        325                 330                 335

TGG TAC GAA CGG GAG GTG ATC CTG CCG GAG CGA TGG ACC CAG GAC CTG        1553
Trp Tyr Glu Arg Glu Val Ile Leu Pro Glu Arg Trp Thr Gln Asp Leu
    340                 345                 350

CGC ACA AGA GTG GTG CTG AGG ATT GGA AGT GCC CAT TCC TAT GCC ATC        1601
Arg Thr Arg Val Val Leu Arg Ile Gly Ser Ala His Ser Tyr Ala Ile
355                 360                 365                 370

GTG TGG GTG AAT GGG GTC GAC ACG CTA GAG CAT GAG GGG GGC TAC CTC        1649
Val Trp Val Asn Gly Val Asp Thr Leu Glu His Glu Gly Gly Tyr Leu
                    375                 380                 385

CCC TTC GAG GCC GAC ATC AGC AAC CTG GTC CAG GTG GGG CCC CTG CCC        1697
Pro Phe Glu Ala Asp Ile Ser Asn Leu Val Gln Val Gly Pro Leu Pro
            390                 395                 400

TCC CGG CTC CGA ATC ACT ATC GCC ATC AAC AAC ACA CTC ACC CCC ACC        1745
Ser Arg Leu Arg Ile Thr Ile Ala Ile Asn Asn Thr Leu Thr Pro Thr
        405                 410                 415

ACC CTG CCA CCA GGG ACC ATC CAA TAC CTG ACT GAC ACC TCC AAG TAT        1793
Thr Leu Pro Pro Gly Thr Ile Gln Tyr Leu Thr Asp Thr Ser Lys Tyr
    420                 425                 430

CCC AAG GGT TAC TTT GTC CAG AAC ACA TAT TTT GAC TTT TTC AAC TAC        1841
Pro Lys Gly Tyr Phe Val Gln Asn Thr Tyr Phe Asp Phe Phe Asn Tyr
435                 440                 445                 450

GCT GGA CTG CAG CGG TCT GTA CTT CTG TAC ACG ACA CCC ACC ACC TAC        1889
Ala Gly Leu Gln Arg Ser Val Leu Leu Tyr Thr Thr Pro Thr Thr Tyr
                    455                 460                 465

ATC GAT GAC ATC ACC GTC ACC ACC AGC GTG GAG CAA GAC AGT GGG CTG        1937
Ile Asp Asp Ile Thr Val Thr Thr Ser Val Glu Gln Asp Ser Gly Leu
            470                 475                 480

GTG AAT TAC CAG ATC TCT GTC AAG GGC AGT AAC CTG TTC AAG TTG GAA        1985
Val Asn Tyr Gln Ile Ser Val Lys Gly Ser Asn Leu Phe Lys Leu Glu
        485                 490                 495

GTG CGT CTT TTG GAT GCA GAA AAC AAA GTC GTG GCG AAT GGG ACT GGG        2033
Val Arg Leu Leu Asp Ala Glu Asn Lys Val Val Ala Asn Gly Thr Gly
    500                 505                 510

ACC CAG GGC CAA CTT AAG GTG CCA GGT GTC AGC CTC TGG TGG CCG TAC        2081
Thr Gln Gly Gln Leu Lys Val Pro Gly Val Ser Leu Trp Trp Pro Tyr
515                 520                 525                 530

CTG ATG CAC GAA CGC CCT GCC TAT CTG TAT TCA TTG GAG GTG CAG CTG        2129
Leu Met His Glu Arg Pro Ala Tyr Leu Tyr Ser Leu Glu Val Gln Leu
                    535                 540                 545

ACT GCA CAG ACG TCA CTG GGG CCT GTG TCT GAC TTC TAC ACA CTC CCT        2177
Thr Ala Gln Thr Ser Leu Gly Pro Val Ser Asp Phe Tyr Thr Leu Pro
            550                 555                 560

GTG GGG ATC CGC ACT GTG GCT GTC ACC AAG AGC CAG TTC CTC ATC AAT        2225
Val Gly Ile Arg Thr Val Ala Val Thr Lys Ser Gln Phe Leu Ile Asn
```

```
                   565                 570                 575
GGG AAA CCT TTC TAT TTC CAC GGT GTC AAC AAG CAT GAG GAT GCG GAC    2273
Gly Lys Pro Phe Tyr Phe His Gly Val Asn Lys His Glu Asp Ala Asp
    580                 585                 590

ATC CGA GGG AAG GGC TTC GAC TGG CCG CTG CTG GTG AAG GAC TTC AAC    2321
Ile Arg Gly Lys Gly Phe Asp Trp Pro Leu Leu Val Lys Asp Phe Asn
595                 600                 605                 610

CTG CTT CGC TGG CTT GGT GCC AAC GCT TTC CGT ACC AGC CAC TAC CCC    2369
Leu Leu Arg Trp Leu Gly Ala Asn Ala Phe Arg Thr Ser His Tyr Pro
            615                 620                 625

TAT GCA GAG GAA GTG ATG CAG ATG TGT GAC CGC TAT GGG ATT GTG GTC    2417
Tyr Ala Glu Glu Val Met Gln Met Cys Asp Arg Tyr Gly Ile Val Val
                630                 635                 640

ATC GAT GAG TGT CCC GGC GTG GGC CTG GCG CTG CCG CAG TTC TTC AAC    2465
Ile Asp Glu Cys Pro Gly Val Gly Leu Ala Leu Pro Gln Phe Phe Asn
                    645                 650                 655

AAC GTT TCT CTG CAT CAC CAC ATG CAG GTG ATG GAA GAA GTG GTG CGT    2513
Asn Val Ser Leu His His His Met Gln Val Met Glu Glu Val Val Arg
                        660                 665                 670

AGG GAC AAG AAC CAC CCC GCG GTC GTG ATG TGG TCT GTG GCC AAC GAG    2561
Arg Asp Lys Asn His Pro Ala Val Val Met Trp Ser Val Ala Asn Glu
675                 680                 685                 690

CCT GCG TCC CAC CTA GAA TCT GCT GGC TAC TAC TTG AAG ATG GTG ATC    2609
Pro Ala Ser His Leu Glu Ser Ala Gly Tyr Tyr Leu Lys Met Val Ile
            695                 700                 705

GCT CAC ACC AAA TCC TTG GAC CCC TCC CGG CCT GTG ACC TTT GTG AGC    2657
Ala His Thr Lys Ser Leu Asp Pro Ser Arg Pro Val Thr Phe Val Ser
                710                 715                 720

AAC TCT AAC TAT GCA GCA GAC AAG GGG GCT CCG TAT GTG GAT GTG ATC    2705
Asn Ser Asn Tyr Ala Ala Asp Lys Gly Ala Pro Tyr Val Asp Val Ile
                    725                 730                 735

TGT TTG AAC AGC TAC TAC TCT TGG TAT CAC GAC TAC GGG CAC CTG GAG    2753
Cys Leu Asn Ser Tyr Tyr Ser Trp Tyr His Asp Tyr Gly His Leu Glu
                        740                 745                 750

TTG ATT CAG CTG CAG CTG GCC ACC CAG TTT GAG AAC TGG TAT AAG AAG    2801
Leu Ile Gln Leu Gln Leu Ala Thr Gln Phe Glu Asn Trp Tyr Lys Lys
755                 760                 765                 770

TAT CAG AAG CCC ATT ATT CAG AGC GAG TAT GGA GCA GAA ACG ATT GCA    2849
Tyr Gln Lys Pro Ile Ile Gln Ser Glu Tyr Gly Ala Glu Thr Ile Ala
            775                 780                 785

GGG TTT CAC CAG GAT CCA CCT CTG ATG TTC ACT GAA GAG TAC CAG AAA    2897
Gly Phe His Gln Asp Pro Pro Leu Met Phe Thr Glu Glu Tyr Gln Lys
                790                 795                 800

AGT CTG CTA GAG CAG TAC CAT CTG GGT CTG GAT CAA AAA CGC AGA AAA    2945
Ser Leu Leu Glu Gln Tyr His Leu Gly Leu Asp Gln Lys Arg Arg Lys
                    805                 810                 815

TAT GTG GTT GGA GAG CTC ATT TGG AAT TTT GCC GAT TTC ATG ACT GAA    2993
Tyr Val Val Gly Glu Leu Ile Trp Asn Phe Ala Asp Phe Met Thr Glu
                        820                 825                 830

CAG TCA CCG ACG AGA GTG CTG GGG ATT AAA AAG GGG ATC TTC ACT CGG    3041
Gln Ser Pro Thr Arg Val Leu Gly Ile Lys Lys Gly Ile Phe Thr Arg
835                 840                 845                 850

CAG AGA CAA CCA AAA AGT GCA GCG TTC CTT TTG CGA GAG AGA TAC TGG    3089
Gln Arg Gln Pro Lys Ser Ala Ala Phe Leu Leu Arg Glu Arg Tyr Trp
            855                 860                 865

AAG ATT GCC AAT GAA ACC AGG TAT CCC CAC TCA GTA GCC AAG TCA CAA    3137
Lys Ile Ala Asn Glu Thr Arg Tyr Pro His Ser Val Ala Lys Ser Gln
                870                 875                 880

TGT TTG GAA AAC AGC CCG TTT ACT TGAGCAAGAC TGATACCACC TGCGTGTCCC    3191
Cys Leu Glu Asn Ser Pro Phe Thr
```

```
Cys Leu Glu Asn Ser Pro Phe Thr
        885             890

TTCCTCCCCG AGTCAGGGCG ACTTCCACAG CAGCAGAACA AGTGCCTCCT GGACTGTTCA    3251

CGGCAGACCA GAACGTTTCT GGCCTGGGTT TTGTGGTCAT CTATTCTAGC AGGGAACACT    3311

AAA                                                                 3314

(2) INFORMATION FOR SEQ ID NO: 2:

(i) SEQUENCE CHARACTERISTICS:
        (A) LENGTH: 909 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Trp Ser Cys Ile Ile Leu Phe Leu Val Ala Thr Ala Thr Gly
-19             -15                 -10                 -5

Val His Ser Gln Val Gln Leu Gln Glu Ser Gly Pro Gly Leu Val Arg
         1               5                  10

Pro Ser Gln Thr Leu Ser Leu Thr Cys Thr Val Ser Gly Phe Thr Ile
         15              20                  25

Ser Ser Gly Tyr Ser Trp His Trp Val Arg Gln Pro Pro Gly Arg Gly
 30              35                  40                  45

Leu Glu Trp Ile Gly Tyr Ile Gln Tyr Ser Gly Ile Thr Asn Tyr Asn
                 50              55                  60

Pro Ser Leu Lys Ser Arg Val Thr Met Leu Val Asp Thr Ser Lys Asn
             65              70                  75

Gln Phe Ser Leu Arg Leu Ser Ser Val Thr Ala Ala Asp Thr Ala Val
         80              85                  90

Tyr Tyr Cys Ala Arg Glu Asp Tyr Asp Tyr His Trp Tyr Phe Asp Val
 95              100                 105

Trp Gly Gln Gly Thr Thr Val Thr Val Ser Ser Gly Gly Gly Gly Ser
110              115                 120                 125

Gly Gly Gly Gly Ser Gly Gly Gly Ser Asp Ile Gln Leu Thr Gln
             130                 135                 140

Ser Pro Ser Ser Leu Ser Ala Ser Val Gly Asp Arg Val Thr Ile Thr
             145                 150                 155

Cys Ser Thr Ser Ser Ser Val Ser Tyr Met His Trp Tyr Gln Gln Lys
         160                 165                 170

Pro Gly Lys Ala Pro Lys Leu Leu Ile Tyr Ser Thr Ser Asn Leu Ala
     175                 180                 185

Ser Gly Val Pro Ser Arg Phe Ser Gly Ser Gly Ser Gly Thr Asp Phe
190                 195                 200                 205

Thr Phe Thr Ile Ser Ser Leu Gln Pro Glu Asp Ile Ala Thr Tyr Tyr
             210                 215                 220

Cys His Gln Trp Ser Ser Tyr Pro Thr Phe Gly Gln Gly Thr Lys Leu
         225                 230                 235

Glu Ile Lys Glu Leu Lys Thr Pro Leu Gly Asp Thr His Thr Cys
     240                 245                 250

Pro Arg Cys Pro Ala Ala Ala Val Gln Gly Met Leu Tyr Pro
     255                 260                 265

Gln Glu Ser Pro Ser Arg Glu Cys Lys Glu Leu Asp Gly Leu Trp Ser
270                 275                 280                 285

Phe Arg Ala Asp Phe Ser Asp Asn Arg Arg Arg Gly Phe Glu Glu Gln
```

-continued

```
                    290                 295                 300
Trp Tyr Arg Arg Pro Leu Trp Glu Ser Gly Pro Thr Val Asp Met Pro
                305                 310                 315
Val Pro Ser Ser Phe Asn Asp Ile Ser Gln Asp Trp Arg Leu Arg His
                320                 325                 330
Phe Val Gly Trp Val Trp Tyr Glu Arg Glu Val Ile Leu Pro Glu Arg
                335                 340                 345
Trp Thr Gln Asp Leu Arg Thr Arg Val Val Leu Arg Ile Gly Ser Ala
350                 355                 360                 365
His Ser Tyr Ala Ile Val Trp Val Asn Gly Val Asp Thr Leu Glu His
                370                 375                 380
Glu Gly Gly Tyr Leu Pro Phe Glu Ala Asp Ile Ser Asn Leu Val Gln
                385                 390                 395
Val Gly Pro Leu Pro Ser Arg Leu Arg Ile Thr Ile Ala Ile Asn Asn
                400                 405                 410
Thr Leu Thr Pro Thr Thr Leu Pro Pro Gly Thr Ile Gln Tyr Leu Thr
                415                 420                 425
Asp Thr Ser Lys Tyr Pro Lys Gly Tyr Phe Val Gln Asn Thr Tyr Phe
430                 435                 440                 445
Asp Phe Phe Asn Tyr Ala Gly Leu Gln Arg Ser Val Leu Leu Tyr Thr
                450                 455                 460
Thr Pro Thr Thr Tyr Ile Asp Asp Ile Thr Val Thr Thr Ser Val Glu
                465                 470                 475
Gln Asp Ser Gly Leu Val Asn Tyr Gln Ile Ser Val Lys Gly Ser Asn
                480                 485                 490
Leu Phe Lys Leu Glu Val Arg Leu Leu Asp Ala Glu Asn Lys Val Val
                495                 500                 505
Ala Asn Gly Thr Gly Thr Gln Gly Gln Leu Lys Val Pro Gly Val Ser
510                 515                 520                 525
Leu Trp Trp Pro Tyr Leu Met His Glu Arg Pro Ala Tyr Leu Tyr Ser
                530                 535                 540
Leu Glu Val Gln Leu Thr Ala Gln Thr Ser Leu Gly Pro Val Ser Asp
                545                 550                 555
Phe Tyr Thr Leu Pro Val Gly Ile Arg Thr Val Ala Val Thr Lys Ser
                560                 565                 570
Gln Phe Leu Ile Asn Gly Lys Pro Phe Tyr Phe His Gly Val Asn Lys
                575                 580                 585
His Glu Asp Ala Asp Ile Arg Gly Lys Gly Phe Asp Trp Pro Leu Leu
590                 595                 600                 605
Val Lys Asp Phe Asn Leu Leu Arg Trp Leu Gly Ala Asn Ala Phe Arg
                610                 615                 620
Thr Ser His Tyr Pro Tyr Ala Glu Glu Val Met Gln Met Cys Asp Arg
                625                 630                 635
Tyr Gly Ile Val Val Ile Asp Glu Cys Pro Gly Val Gly Leu Ala Leu
                640                 645                 650
Pro Gln Phe Phe Asn Asn Val Ser Leu His His Met Gln Val Met
                655                 660                 665
Glu Glu Val Val Arg Arg Asp Lys Asn His Pro Ala Val Val Met Trp
670                 675                 680                 685
Ser Val Ala Asn Glu Pro Ala Ser His Leu Glu Ser Ala Gly Tyr Tyr
                690                 695                 700
Leu Lys Met Val Ile Ala His Thr Lys Ser Leu Asp Pro Ser Arg Pro
                705                 710                 715
```

```
Val Thr Phe Val Ser Asn Ser Asn Tyr Ala Ala Asp Lys Gly Ala Pro
        720                 725                 730
Tyr Val Asp Val Ile Cys Leu Asn Ser Tyr Tyr Ser Trp Tyr His Asp
        735                 740                 745
Tyr Gly His Leu Glu Leu Ile Gln Leu Gln Leu Ala Thr Gln Phe Glu
750                 755                 760                 765
Asn Trp Tyr Lys Lys Tyr Gln Lys Pro Ile Ile Gln Ser Glu Tyr Gly
                770                 775                 780
Ala Glu Thr Ile Ala Gly Phe His Gln Asp Pro Pro Leu Met Phe Thr
            785                 790                 795
Glu Glu Tyr Gln Lys Ser Leu Leu Glu Gln Tyr His Leu Gly Leu Asp
        800                 805                 810
Gln Lys Arg Arg Lys Tyr Val Val Gly Glu Leu Ile Trp Asn Phe Ala
        815                 820                 825
Asp Phe Met Thr Glu Gln Ser Pro Thr Arg Val Leu Gly Asn Lys Lys
830                 835                 840                 845
Gly Ile Phe Thr Arg Gln Arg Gln Pro Lys Ser Ala Ala Phe Leu Leu
                850                 855                 860
Arg Glu Arg Tyr Trp Lys Ile Ala Asn Glu Thr Arg Tyr Pro His Ser
            865                 870                 875
Val Ala Lys Ser Gln Cys Leu Glu Asn Ser Pro Phe Thr
            880                 885                 890

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ACCAGAAGCT TATGAATATG CAAATC                                            26

(2) INFORMATION FOR SEQ ID NO: 4:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

GCCACCCGAC CCACCACCGC CCGATCCACC GCCTCCTGAG GAGACGGTGA CCGTGGTC         58

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GGTGGATCGG GCGGTGGTGG GTCGGGTGGC GGCGGATCTG ACATCCAGCT GACCCAGAGC       60
```

(2) INFORMATION FOR SEQ ID NO: 6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
TGCAGGATCC AACTGAGGAA GCAAAGTTTA AATTCTACTC ACCTTTGATC          50
```

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
TTTTTAAGCT TAGATCTCCA CCTTGGTC                                 28
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
AAAAATCTAG AATGCAGGTC CAACTGCAGG AGAG                          34
```

(2) INFORMATION FOR SEQ ID NO: 9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
AAAAAAGTGA TCAAAGCGTC TGGCGGGCCA CAGGGCGGGA TCCTGTAC            48
```

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
TTTTAAGCTT CAAGTAAACG GGCTGTT                                  27
```

(2) INFORMATION FOR SEQ ID NO: 11:

(i) SEQUENCE CHARACTERISTICS:

(A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

TTTTGGTACC TTTGGATAAA AGACAGGTCC AACTGCAGGA GAG                43

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

AAAACCATGG GAATTCAAGC TTCGAGCTGG TACTACAGGT                    40

(2) INFORMATION FOR SEQ ID NO: 13:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

TTTTAAGCTT CCATGGCGGC CGCTCATTGT TTGCCTCCCT GCTG               44

(2) INFORMATION FOR SEQ ID NO: 14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

AAAAAGATCT CCGCGTCTGG CGGGCCACAG TTACGTGTAG AAACCCCA           48

(2) INFORMATION FOR SEQ ID NO: 15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

TTTTGGTACC TTTGGATAAA AGACAGGTCC AACTGCAGGA GAG                43

(2) INFORMATION FOR SEQ ID NO: 16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued

```
    (ii) MOLECULE TYPE: DNA (genomic)

(xi) SEQUENCE DESCRIPTION: SEQ ID NO: 16:

AAAAAGCTTA GATCTCCAGC TTGGTCCC                                                28

(2) INFORMATION FOR SEQ ID NO: 17:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

AAAGAATTCT GATCAAATCC TCGAGCTCAG GTTCACAAAA GGTAGAGAAA ACAGT              55

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

TTTAAGCTTA TTTTAATAAA TCCAATGT                                                28
```